United States Patent
Jaqueth et al.

(10) Patent No.: US 11,649,466 B2
(45) Date of Patent: *May 16, 2023

(54) GENETIC LOCI ASSOCIATED WITH RESPONSE TO ABIOTIC STRESS

(71) Applicants: CORTEVA AGRISCIENCE LLC, Indianapolis, IN (US); PIONEER HI-BRED INTERNATIONAL, INC., Johnston, IA (US)

(72) Inventors: Jennifer S Jaqueth, Des Moines, IA (US); Bailin Li, Johnston, IA (US); Zhizeng Liu, Xinxiang (CN)

(73) Assignees: CORTEVA AGRISCIENCE LLC, Indianapolis, IN (US); PIONEER HI-BRED INTERNATIONAL, INC.

( * ) Notice: Subject to any disclaimer, the term of this patent is extended or adjusted under 35 U.S.C. 154(b) by 52 days.

This patent is subject to a terminal disclaimer.

(21) Appl. No.: 16/843,295

(22) Filed: Apr. 8, 2020

(65) Prior Publication Data
US 2020/0231982 A1 Jul. 23, 2020

Related U.S. Application Data

(63) Continuation of application No. 15/039,210, filed as application No. PCT/US2014/067335 on Nov. 25, 2014, now Pat. No. 10,683,515.

(60) Provisional application No. 61/950,345, filed on Mar. 10, 2014, provisional application No. 61/909,565, filed on Nov. 27, 2013.

(51) Int. Cl.
*C12N 15/82* (2006.01)
*C07K 14/415* (2006.01)
*A01H 6/46* (2018.01)
*A01H 5/10* (2018.01)

(52) U.S. Cl.
CPC ........... *C12N 15/8273* (2013.01); *A01H 5/10* (2013.01); *A01H 6/4684* (2018.05); *C07K 14/415* (2013.01)

(58) Field of Classification Search
None
See application file for complete search history.

(56) References Cited

U.S. PATENT DOCUMENTS

2002/0083485 A1 6/2002 Zhu et al.
2009/0094717 A1* 4/2009 Troukhan ............. C12Q 1/6895
800/290

FOREIGN PATENT DOCUMENTS

WO 2009134339 A2 11/2009

OTHER PUBLICATIONS

Fageria, (Plant and soil 88.2 (1985): 237-243). (Year: 1985).*
Feki et al. (Plant Cell Rep (2014) 33:277-288). (Year: 2014).*
Ishimaru, et al. "Identification of a new gene controlling plant height in rice using the candidate-gene strategy." Planta 218.3 (2004): 388-395. (Year: 2004).*
Beatriz Estrada et al "Arbuscular mycorrhizal fungi native from a Mediterranean saline area enhance maize tolerance to salinity through improved ion homeostasis" Plant Cell & Environment vol. 36 No. 10 pp. 1771-1782.
GenBank Accession No. AF256224, dated Jun. 14, 2000. (Year: 2000).
GenBank Accession No. NM 101333, dated Jun. 9, 2006. (Year: 2006).
Guo, et al. (2004, Proc. Natl. Acad. Sci. USA 101: 9205-9210). (Year: 2004).
Kaouthar Feki et al "A constitutively active form of a durum wheat Na+/H+ antiporter SOS1 confers high salt tolerance to transgenic *Arabidopsis*" Plant Cell Reports vol. 33. No. 2. Oct. 23, 2013 (Oct. 23, 2013). pp. 277-288.
Shi, et al. (Nature Biotechnology 21.1 (2003):81). (Year: 2003).
Toshio Yamaguchi et al: "Sodium transport system in plant cells" Frontiers in Plant Science vol. 4. Jan. 1, 2013 (Jan. 1, 2013) p. 1-7.
Wang, Shilei et al "Mapping of QTLs Associated with Salt Tolerance of Maize Inbred Line at Seedling Stage", Agricultural Biotechnology vol. 1(4) 2012 p. 34-38.
International Search Report and Written Opinion for International Application No. PCT/US2014/067335, dated May 22, 2015.

* cited by examiner

*Primary Examiner* — Charles Logsdon

(57) ABSTRACT

Compositions and methods useful in identifying and counter-selecting maize plants with having enhanced yield-related traits relative to control plants under abiotic stress conditions such as salt stress and/or drought are provided herein. The methods use molecular genetic markers to identify, select and/or construct salt stress tolerant and/or drought tolerant maize plants. Also provided are methods to enhance tolerance to salt stress and/or drought in crop plants by transforming crop plants with the *Zea mays* antiporter/sodium ion transporter or by introducing favorable allelic variants of the *Zea mays* antiporter/sodium ion transporter gene via gene editing.

4 Claims, 9 Drawing Sheets

Figure 1A:
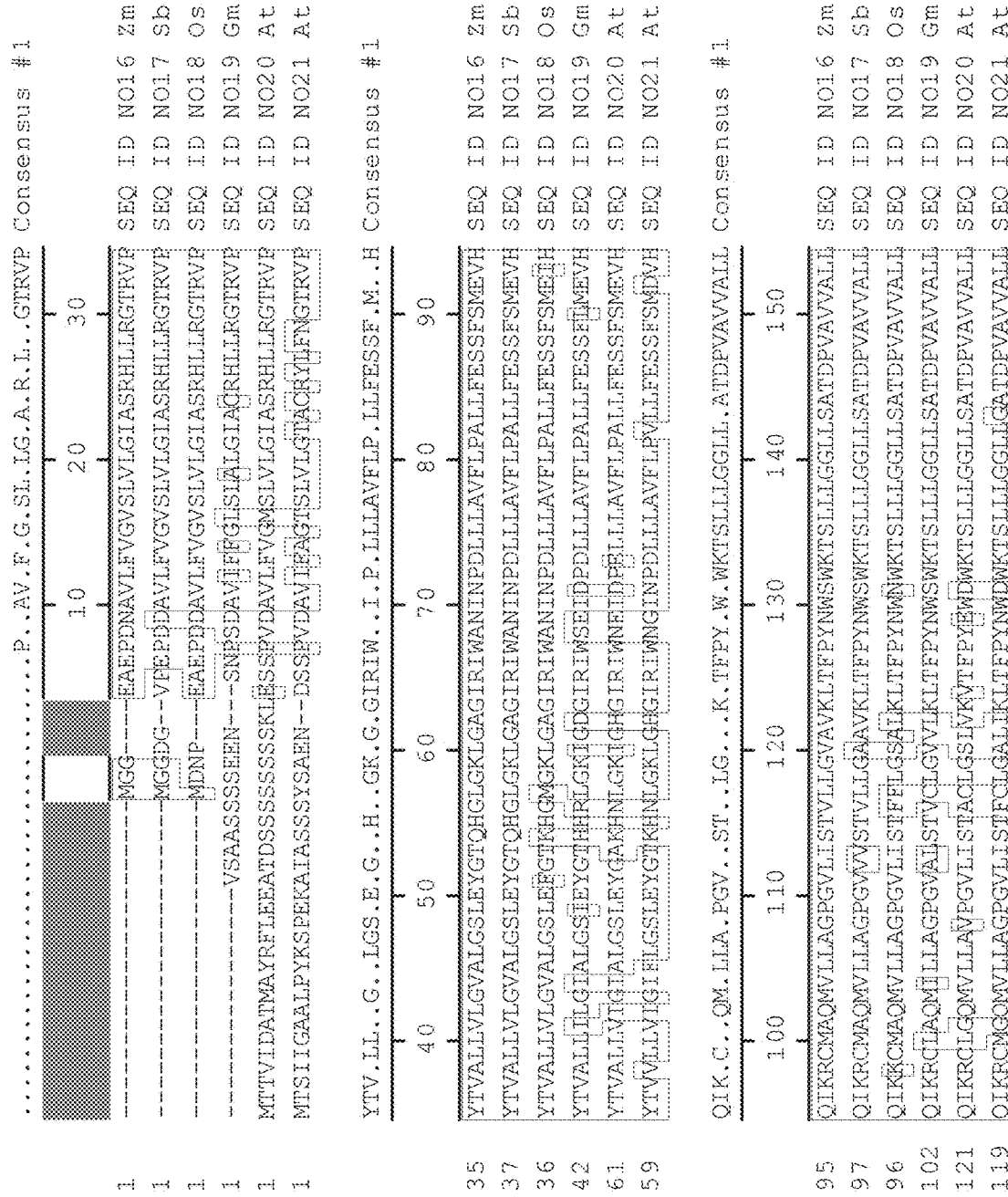

Specification includes a Sequence Listing.

FIG. 1B

```
       K.LGASKK..T.I.GESLMNDG...V...LF.M..G......IIKFL.....GAV..G  Consensus #1
              160       170       180       190       200       210
              |         |         |         |         |         |
155  KELGASKKLSTIIEGESLMNDGTAIVAYQLFYRMVLGRTFDAGSIIKFLSEVSLGAVALG   SEQ ID NO16 Zm
157  KELGASKKLSTIIEGESLMNDGTAIVVYQLFYRMVLGRTFDAGSIIKFLSEVSLGAVALG   SEQ ID NO17 Sb
156  KELGASKKLSTIIEGESLMNDGTAIVVYQLFYRMVLGRTFDAGSIIKFLSEVSLGAVALG   SEQ ID NO18 Os
162  KDLGASKKLSTIIEGESLMNDGTAIVVYTLFYRMVLGETFNWVAIIKFLAQVSLGAVGMG   SEQ ID NO19 Gm
181  KELGASKKLSTIIEGESLMNDGTAIVVFQLELKMAMGQNSDWSSIIKFLILKVALGAVGIG  SEQ ID NO20 At
179  KELGASKFMTLJDGESLMNDGVSVMVFQLEFRMVMGHNSDWGSIIKFLVQNSFGAVGIG    SEQ ID NO21 At LAFGI.S..WL.FIFNDT....I..T...SY.A..TAQ......SG.LTVM.LGMF..AFA. Consensus #1
              220       230       240       250       260       270
              |         |         |         |         |         |
215  LAFGIMSIILMLGFIFNDTIIEIALTLAVSYIAFFTAQDSLEVSGVLTVMTLGMFYAAFAK   SEQ ID NO16 Zm
217  LAFGIMSIILMLGFIFNDTIIEIALTLAVSYIAFFTAQDSLEVSGVLTVMTLGMFYAAFAK   SEQ ID NO17 Sb
216  LAFGIASVLMLGFIFNDTIIEIALTLAVSYIAFFTAQDALEVSGVLTVMTLGMFYAAFAK   SEQ ID NO18 Os
222  LAFGIASVLWLGFIFNDTVIEIALTFAVSYIAYFTAQEGSGVSGVLTVMSLGMFYSAAFAR  SEQ ID NO19 Gm
241  LAFGIASVIMIKFIENDTVIEITLTFIAVSYFAYYTAQEWAGASGVLTVMTLGMFYAAFAR  SEQ ID NO20 At
239  LAFGIASVFMIKFIFNDTVAQITVTISASYFAYYTAQEWAGVSGILTVMILGMFFAAFAR  SEQ ID NO21 At TAFKG.S..SLHHFW...... Consensus #1
              280       290       300       310       320       330
              |         |         |         |         |         |
275  TAFKGESQQSLHHFWFKVQTQSWFLTLAAVRQYHCVKVPQDFKGFLDLFAPGDYLTPIGQ  SEQ ID NO16 Zm
277  TAFKGESQQSLHHFW---------------------------------------------   SEQ ID NO17 Sb
276  TAFKGBSQQSLHHFW---------------------------------------------   SEQ ID NO18 Os
282  TAFKGESQQSLHHFW---------------------------------------------   SEQ ID NO19 Gm
301  TAFKGDSQKSLHHFW---------------------------------------------   SEQ ID NO20 At
299  TAFKGDSHQSLHHFW---------------------------------------------   SEQ ID NO21 At
```

FIG. 1D

```
         L.MD.L...K.RIL..T..EM...AL..F..L.DDEELG..ADW.TV...I..L........ Consensus #1
              500       510       520       530       540       550
         LGMDKLLPTKLRILKYTRYEMLKKALEAFGELRDDEELG-PADWTVKKYITCLNDLDYE  SEQ ID NO16 Zm
    492  LSMDKISATKLRILKYTRYEMINKALESFGELRDDEELG-PADWTVKKYITCLNDLDNE  SEQ ID NO17 Sb
    430  LGMDRIAATKLRITNYTKYEMINKALEAFGDLRDDEELGPPADWTVKKYITCLNDLDDE  SEQ ID NO18 Os
    429  LGMDKISAAKRRIINFTKYEMINKALEAFGEIGDDEELG-PADWPTVKRYISCLNDIEGE SEQ ID NO19 Gm
    457  LRMDTHPAPKRILEYTRYEMINKAIRAFQDLGDDEELG-PADWPTVESYISSLKGSEGE  SEQ ID NO20 At
    451  LRMDTHTATKKRILEYTKFEMMKTALKAFENLGDDEELG-SADWPTVIRHISSLKDLEGR SEQ ID NO21 At
    449

....PH................DIR.R.LNGVQA.YW.ML..GRI..TAN.LM.SV.EA. Consensus #1
              560       570       580       590       600
         PEH-PHDVGDEDDCMHIMNLTDIRVRLLNGVQAAYWGMLEEGRITQVTANIILMRSVDEAM SEQ ID NO16 Zm
    551  PEH-PHDVSGKDDHMHIMNLTDIRVRLLNGVQAAYWGMLEEGRITQATANIILMRSVDEAM SEQ ID NO17 Sb
    489  PVH-PHAVSBRNDRMHTMNLRDIRVRLLNGVQAAYWGMLEEGRITQTTANIILMSVEEAV SEQ ID NO18 Os
    489  CVH-PHGAPENDSNLDPMNLKDIRVRLLNGVQAAYWEMIDEGRISQTTANIILMSVEEAV  SEQ ID NO19 Gm
    516  LVHHPHNGSKIGS-LDPKSLKDIRMRFLNGVQATYWEMIDEGRISFVTANIILMQSVDEAL SEQ ID NO20 At
    510  QVN-PHDGYEAGS-LDPTNIMDIRIREFLNGVQAAYWEMIDDGRITQCTANVLMQSVDEAL SEQ ID NO21 At
    508

D.......L.DW.GL.....V.FPNYY.FL......P..L.T....VERLES.CYI..AFLRAH. Consensus #1
              620       630       640       650       660
         DLVSGQTLCIDWKGLKSNVQFPNYYRFLQRSRLPRKIVTYFTVERLESGCYICAAFLRAHR SEQ ID NO16 Zm
    610  DIVSEQKILCDWKGLKSNVQFPNYYRFLQMSRLPRKIVTYFTVERLESGCYICAAFLRAHR SEQ ID NO17 Sb
    548  DLVPTQELCDWKGLESNVHFPNYYRFLQMSRLPRHITYFTVERLESGCYICAAFLRAHR   SEQ ID NO18 Os
    548  DLASSEPLCDWKGLKSNVHFPNYYKFLQSMFPRKLVTYFTVERLESACYICAAFLRAHR   SEQ ID NO19 Gm
    575  DQVSTT-LCDWRGLKPHVNFPNYYNFTHSKVVPRKLVTYFAVERLESACYISAAFLRAHT  SEQ ID NO20 At
    569  DLVSTSSLSDWRGLEPRVHFPNYYKFLQSKIIBHKLVTHLIVERLESACYISSAFLRAHR  SEQ ID NO21 At
    566
```

FIG. 1E

```
       IAR.QL..F.G.S.....VI.ES..EGEEA..FLE.V....PQVL.V.KT.Q.T..VL.H Consensus #1
              670       680       690       700       710       720
670   IARRQLHDFLGDSEVARTVIDESNAEGEEARKFLEDVRVTFPQVLRVLKTRQVFTYSVLTH  SEQ ID NO16 Zm
608   IARRQLHDFLGDSEVARTVIDESNAEGEEARKFLEDVRVTFPQVLRVLKTRQVTYSVLTH   SEQ ID NO17 Sb
608   IARRQLHDFLGDSEVARIVIDESNAEGEEARKFLEDVRVTHPQVLRVLKTRQVTYSVLTH   SEQ ID NO18 Os
635   IARQLHDFIGDSDIASAVINESVVEGEEARKFLEDVNTYPQVLRVMKTRQATYAVINH    SEQ ID NO19 Gm
628   IARQQHYDFLGESNIGSIVINESEKEGEEAKFLEKVRSSFPQVLRVMKTIQVTYSVINH   SEQ ID NO20 At
626   IARQQLHIFLGNSNTASTVINESEVEGEEAKQFLEDVSFPQVLSVLKTRQVTHAVINH    SEQ ID NO21 At L..Y...NL.K.G.LE.KE....L.D..Q..LKK..R.PP..K.P.............  Consensus #1
              730       740       750       760       770       780
730   LSEYIQNLQKTGLLEEKEMVHLDDALQTDLKKLQRNPPIVKMPRVSDLLNTHPLVGALPA  SEQ ID NO16 Zm
668   LSEYIQNLQKTGLLEEKEMVQLDDALQTDLKKLQRNPPIVKMPRVSDLLNTHPLVGALPA  SEQ ID NO17 Sb
668   LSEYIQNLQKTGLLEEKEMAHLDDALQTDLKKFFRNPPIVKMPRVSDLLNTHPLVGALPA  SEQ ID NO18 Os
695   LIEYVENLEEKAGILEEKEMLQIHEDAVQTDLKKILRNPPIVKLIPKISSIHPMLG---ALPS  SEQ ID NO19 Gm
688   LLGYIENLEEKVGLLEEKEIAHLHDAVQTGLKKLLRNPPIVHLPKLSEMITSHPLSVALEP  SEQ ID NO20 At
686   LNGYIKNLEERVGLLEGKEVSHLHDVVQSDLKKILHHPPSLKLIPNVDDLITSN------  SEQ ID NO21 At ...........................................................  Consensus #1
              790       800       810       820       830       840
790   AVRDTLLSNTKETILRGQGTTLYREGSRPTGIWLVSIGVVKWTSQRLSRRHSLDPIILSHGS  SEQ ID NO16 Zm
728   AVRDPLLSNTKETVRGQGTTLYREGQGTTLYREGSRPTGIWLVSIGVVKWTSQRLSRRHCLDPILSHGS  SEQ ID NO17 Sb
728   AMRDPLLSSTKETVKGHGTIYREGTIYREGSRPTGIWLVSIGVVKWTSQRLSSRHSLDPILSHGS  SEQ ID NO18 Os
752   SVRESIASCTKEMMKLRGLITLYKEGAKSNGIWLIHSNGVVKWESKMIRIPKHSFNPTFHGS  SEQ ID NO19 Gm
748   AFCEPLKHSKKEPMKLLRGVTLYKEGSKPTGVWLIFDGIVKWKSKIILSNNHSLHPTFSHGS  SEQ ID NO20 At
738   ---------------------------------------PL-----------------   SEQ ID NO21 At
```

FIG. 1G

```
                   . . . . | . . . . | . . . . | . . . . | . . . . | .
                       1020         1030         1040         1050         1060
Consensus #1                                                LAAEMLPGGLSSRALQ
1018 ASLPQG------EPARSMSKEHSGLLSWPESFRRSRGSLG----LAAEMLPGGLSSRALQ     SEQ ID NO16 Zm
 953 LLLPQGQ-GGGHEPTRSMSKEHSGLLSWPESFRRSRGNLG----LAAEMLPGGLSSRALQ     SEQ ID NO17 Sb
 963 SLISQT------LELPRTQSKEHSGLLSWPESFRKSRGAQNGASLTEIRDHRASFSARALQ    SEQ ID NO18 Os
 991 SSELS-------HAGDHPHRSFRRKHSGIMSWPEHFYKQDHKQRSE----GRAGRQTNSLSARAMQ SEQ ID NO19 Gm
 986 SSETPPRSSSSDQLQRSFKEHRGLMSWPENIYAKQQQEIN--------KTTLSLSERAMQ    SEQ ID NO20 At
 756                                                                SEQ ID NO21 At . . . . | . . . . | . . . . | . . . . | . . . . | .
                       1070         1080         1090         1100         1110         1120
Consensus #1                                                                    KERHLLSV
1068 LSMYGGSVVSLSSGQQGHRRQRPRHRVQAATTMFNQKKHSSSYPRMPSIS---KERHLLSV    SEQ ID NO16 Zm
1008 LSMYG-SMILSGQGHSHRPQGRHRVQATTTDQ---RQSSYPRMPSIS--KERPLLSV       SEQ ID NO17 Sb
1018 LSMYGSMTNDMKSGQGQGRRQ-RHRHTKASSNK---AHSSSYPRVPSRSNTQRPLLSV      SEQ ID NO18 Os
1045 LSIYGSMMFFINVENQIP-DHTLKRQCYLSSMPH----------HIG-----VCRPHVSV    SEQ ID NO19 Gm
1039 LSIFGSMVNVYRRSVSFGGIYNNKLQDNLLYKKL--------------RLN--------PAQGHVSA SEQ ID NO20 At
 756                                                                SEQ ID NO21 At . . . . | . . . . | . . . . | . . . . | . . . . | .
                       1130         1140         1150         1160         1170         1180
Consensus #1
1126 QSEGSNMK---RVAALP--EVAATAPAPAGAAQGQRRAMLQEEYNSSEDSAGEEVIVRVD    SEQ ID NO16 Zm
1062 QSEGSNMK---RVAALPLRDDRAEVEAPAAQQRRFRKAMFLQED--NSSDDSAGEEVIVRVD   SEQ ID NO17 Sb
1074 QSEGANMTTAPQAAAAGASLPPEPEEAGRRRRRRQRKAIEEDED--NSSDESAGEEVIVRVD   SEQ ID NO18 Os
1089 KSEGAATA----KKVHEVTRHVTRVTNPPSQSTERRQHHHGDNSSDD-------SGAEEEDIIVRID SEQ ID NO19 Gm
1084 KSESSIVT----KKQEETRKHACQLPLKGESSTFQNTMVESSDE------E-DEDEGIVRID  SEQ ID NO20 At
 756                                                                SEQ ID NO21 At
```

FIG. 1H

```
                                            Consensus #1
                                            SEQ ID NO16 Zm
                                            SEQ ID NO17 Sb
                                            SEQ ID NO18 Os
                                            SEQ ID NO19 Gm
                                            SEQ ID NO20 At
                                            SEQ ID NO21 At
```

```
           1190       1200
1182  SPSMLSFRESTAVPPPQEQ
1119  SPSMLSFRQSAAAPPPQDQ
1133  SPSMLTFRQPSSAADR
1142  SPSTLSFR
1136  SPSKIVFRNDL
 756
```

FIG. 2

| | 1 | 2 | 3 | 4 | 5 | 6 | | |
|---|---|---|---|---|---|---|---|---|
| 1 |  | 86.2 | 77.2 | 57.4 | 55.3 | 51.8 | 1 | SEQ ID NO 16 Zm |
| 2 | 9.1 |  | 83.0 | 62.9 | 60.0 | 58.5 | 2 | SEQ ID NO 17 Sb |
| 3 | 20.5 | 19.2 |  | 62.0 | 60.4 | 58.3 | 3 | SEQ ID NO 18 Os |
| 4 | 49.5 | 49.4 | 51.3 |  | 63.8 | 58.3 | 4 | SEQ ID NO 19 Gm |
| 5 | 54.4 | 56.6 | 54.7 | 48.0 |  | 67.1 | 5 | SEQ ID NO 20 At |
| 6 | 46.4 | 46.4 | 46.5 | 43.1 | 31.5 |  | 6 | SEQ ID NO 21 At |
|  | 1 | 2 | 3 | 4 | 5 | 6 | | |

Percent Identity

GENETIC LOCI ASSOCIATED WITH RESPONSE TO ABIOTIC STRESS

CROSS REFERENCE TO RELATED APPLICATIONS

This application is a continuation of U.S. non-provisional application Ser. No. 15/039,210 filed on May 25, 2016, now granted U.S. Pat. No. 10,683,515; which is a national stage entry from international application number PCT/US2014/067335, filed Nov. 25, 2014, which claims the benefit of and priority to U.S. Provisional Application No. 61/909,565, filed Nov. 27, 2013, and of U.S. Provisional Application No. 61/950,345, filed Mar. 10, 2014, the entire contents of which are herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20141118_BB2241PCT_SequenceListing_ST25 created on Nov. 18, 2014 and having a size of 144 kilobytes and is filed concurrently with the specification. The sequence listing contained in this ASCII formatted document is part of the specification and is herein incorporated by reference in its entirety.

FIELD

The field is related to plant breeding and methods of generating maize plants expressing enhanced yield related traits under abiotic stress conditions such as salt stress and/or drought.

BACKGROUND

Abiotic stressors such as drought, salinity, cold, flood and chemical pollution significantly limit crop production worldwide. Cumulatively, these factors are estimated to be responsible for an average 70% reduction in agricultural production. Soil salinity is an abiotic stress that impacts crop yield worldwide and restricts the use of otherwise arable land (Zia et al. 2011. *Journal of Medicinal Plants Research.* 5(25):6040-6047). However, there are currently no economically sustainable and effective methods for overcoming problems associated with soil salinity as it relates to crop production.

Several studies have shown that the effects of cytotoxicity induced by salt stress can be ameliorated by the exogenous application of chemical compounds such as glycerol (Kaya et al. 2013. *Acta Botanica Croatica* 72(1):157-168); salicylic acid (Tufail et al. 2013. *Pakistan Journal of Botany* 45(1):75-82); and kinetin [KIN] and indoleacetic acid [IAA] (Kaya et al. 2010. *Turkish Journal of Agriculture and Forestry* 34(6):529-538; Kaya et al. 2010. *Journal of Plant Nutrition.* 33(3):405-422). Other studies have shown that when phosphorous supply is sufficient, inoculation with fungus enhances salinity tolerance by other mechanisms (Gu et al. 2000. *Journal of Plant Resources and Environment.* 9(2):22-26).

Another approach is production of salt tolerant transgenic plants through incorporation of salt tolerant genes such as the TaHAK1gene (YuXiang et al. 2011. *Journal of Triticeae Crops* 31(6):1014-1019), the AtSAT32 gene (MinYoung et al. 2009. *Physiologia Plantarum* 135(4):426-435.), and the MBF1a gene (MinJung et al. 2007. *Biochemical and Biophysical Research Communications.* 354(2):440-446.).

Still other studies have suggested that seed priming with NaCl may be a reliable procedure to increase the maize salinity tolerance (Frahbakhsh and Saiid. 2011. *African Journal of Agricultural Research.* 6(28):6095-6099.).

Breeding new salt tolerant maize varieties presents an effective way to improve the total output of maize and to use salinized soil effectively (Dong et al. 2010. *Chinese Agricultural Science Bulletin.* 26(10):246-249; Nitsch, J P. 1950. *Am J Botany.* 37:211-215). However, salt tolerance is a complex trait which is difficult to breed for in plants.

SUMMARY

Compositions and methods for identifying and counter-selecting maize plants with increased susceptibility to high salt soils (salt stress) and/or drought stress are provided herein. The methods are also useful in identifying and selecting maize plants that have increased tolerance to salt stress and/or drought stress. Methods are also provided that can be used to generate plants with increased tolerance to salt stress and/or drought stress.

In one embodiment, methods of identifying maize plants with decreased tolerance to salt stress and/or drought are presented herein. In these methods, a QTL allele is detected in a maize plant, wherein the QTL allele is associated with decreased tolerance to salt stress and/or drought and comprises a 4 bp deletion in the *Zea mays* antiporter/sodium ion transporter gene at nucleotides 3311-3314 of SEQ ID NO:15. A maize plant is then identified as having the QTL allele if the deletion is present. The method may further include counter-selecting a maize plant from a breeding program if the QTL allele is detected or selecting a maize plant if the QTL allele is not detected.

In another embodiment, methods of identifying maize plants with tolerance to salt stress and/or drought are provided in which any of the following are detected in the genome of a maize plant: a polynucleotide encoding a polypeptide having the amino acid sequence set forth in SEQ ID NO:16; a polynucleotide encoding a polypeptide having an amino acid sequence that is at least 80% identical to SEQ ID NO:16 that has antiporter/sodium ion transporter activity; or one or more marker alleles within 5 cM of (i) or (ii) that are linked to and associated with (i) or (ii); and maize plants having any of (i), (ii), or (iii) are identified as having tolerance to salt stress and/or drought.

In another embodiment, a method of increasing tolerance to salt stress and/or drought in a plant is presented in which a recombinant DNA construct comprising a polynucleotide operably linked to at least one regulatory sequence, wherein the polynucleotide encodes a polypeptide having an amino acid sequence of at least 80%, 85%, 90%, 95% or 100% sequence identity, based on the Clustal V method of alignment, when compared to SEQ ID NO:16, 17, 18, 19, 20, or 21, is introduced into a regenerable plant cell. A transgenic plant is then regenerated from the regenerable plant cell and the transgenic plant has the recombinant DNA construct in its genome. The transgenic plant exhibits increased tolerance to salt stress and/or drought when compared to a control plant not comprising the recombinant DNA construct.

The method may further comprise obtaining progeny plants from the transgenic plants that also comprise the recombinant DNA construct and exhibit increased tolerance to salt stress and/or drought when compared to a control plant without the recombinant DNA construct.

The recombinant DNA construct may contain at least one regulatory element that may be a promoter. In some instances, the promoter may be a root-specific promoter.

The plants may be *Arabidopsis*, maize, soybean, sunflower, sorghum, canola, wheat, alfalfa, cotton, rice, barley, millet, sugar cane, or switchgrass. In some instances, the plant is a monocot, and in still further instances, the plant is maize.

In another embodiment, methods of increasing tolerance to salt stress and/or drought in a plant are presented in which a recombinant polynucleotide that encodes a polypeptide having an amino acid sequence of at least 80% sequence identity, based on the Clustal V method of alignment, when compared to SEQ ID NO:16, 17, 18, 19, 20, or 21 is expressed in a plant and tolerance to salt stress and/or drought in the plant is increased as compared to a control plant not comprising the recombinant polynucleotide. The methods may further comprise obtaining a progeny plant derived from the plant expressing the recombinant polynucleotide, wherein said progeny plant comprises in its genome the recombinant polynucleotide and exhibits increased tolerance to salt stress and/or drought when compared to a control plant not comprising the recombinant polynucleotide.

The plants may be *Arabidopsis*, maize, soybean, sunflower, sorghum, canola, wheat, alfalfa, cotton, rice, barley, millet, sugar cane, or switchgrass. In some instances, the plant is a monocot, and in still further instances, the plant is maize.

In another embodiment, methods of identifying variants of the maize antiporter/sodium ion transporter gene or variants of the genes encoding orthologous proteins wherein the variants have an effect on the abiotic stress tolerance phenotype are provided. In these methods, one or more nucleotide sequences encoding one or more fragments of SEQ ID NO:16, 17, 18, 19, 20, or 21, or a protein that is at least 80%, 85%, 90%, 95% or 100% identical to SEQ ID NO:16, 17, 18, 19, 20, 21, or 22 or a fragment thereof, are combined through gene shuffling to generate variants that exhibit increased tolerance to salt stress and/or drought when expressed in plants. The methods may further comprise introducing recombinant DNA constructs containing the variants that exhibited increased tolerance to salt stress and/or drought into regenerable plant cells to obtain transgenic plants with increased tolerance to salt stress and/or drought.

The transgenic plants may be *Arabidopsis*, maize, soybean, sunflower, sorghum, canola, wheat, alfalfa, cotton, rice, barley, millet, sugar cane, or switchgrass. In some instances, the plant is a monocot, and in still further instances, the plant is maize.

In another embodiment, methods of identifying allelic variants of the maize antiporter/sodium ion transporter gene that are associated with increased tolerance to salt stress and/or drought are provided herein. In these methods, a population of maize plants is obtained in which the maize plants have differing levels of salt stress tolerance and/or drought tolerance. Allelic variations are evaluated with respect to SEQ ID NO:15, or the genomic regions that regulate the expression of this gene. Allelic variations can then be identified as being associated with increased tolerance to salt stress and/or drought. The method may further include selecting for said allelic variation as part of a maize breeding program or introducing the allelic variant into a target site in the genome of a maize plant cell. The introducing step may occur by way of nucleases such as but not limited to: zinc finger nuclease, Transcription Activator-like Effector Nuclease (TALEN), the CRISPR/Cas system, and meganuclease.

A recombinant DNA construct comprising a polynucleotide operably linked to at least one regulatory sequence wherein said polynucleotide comprises a nucleic acid sequence encoding an amino acid sequence of at least 80%, 85%, 90%, 95% or 100% sequence identity, based on the Clustal V method of alignment, when compared to SEQ ID NO:16, 17, 18, 19, 20, or 21, is also provided. The regulatory sequence may be any promoter functional in a plant cell. Also provided are transgenic plant cells, plants, and seeds containing the recombinant DNA constructs. The plant may be *Arabidopsis*, maize, soybean, sunflower, sorghum, canola, wheat, alfalfa, cotton, rice, barley, millet, sugar cane, or switchgrass.

Maize plants that display tolerance or improved tolerance to one or more abiotic stress conditions such as salt and/or drought stress as generated by the methods disclosed herein are also provided.

BRIEF DESCRIPTION OF THE DRAWINGS AND SEQUENCE LISTING

The invention can be more fully understood from the following detailed description and the accompanying drawings and Sequence Listing which form a part of this application.

Figure 1C:
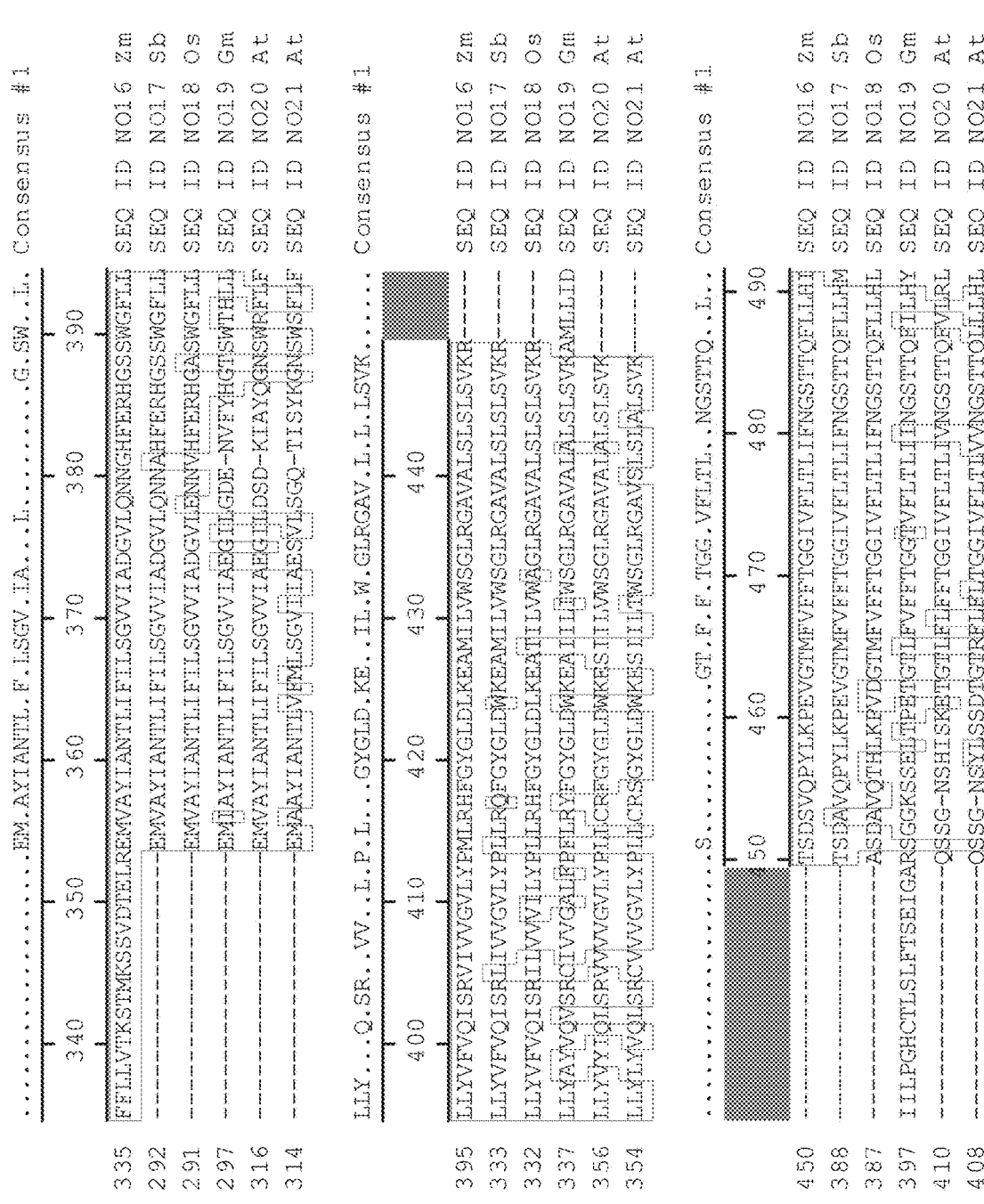
Figure 1F:
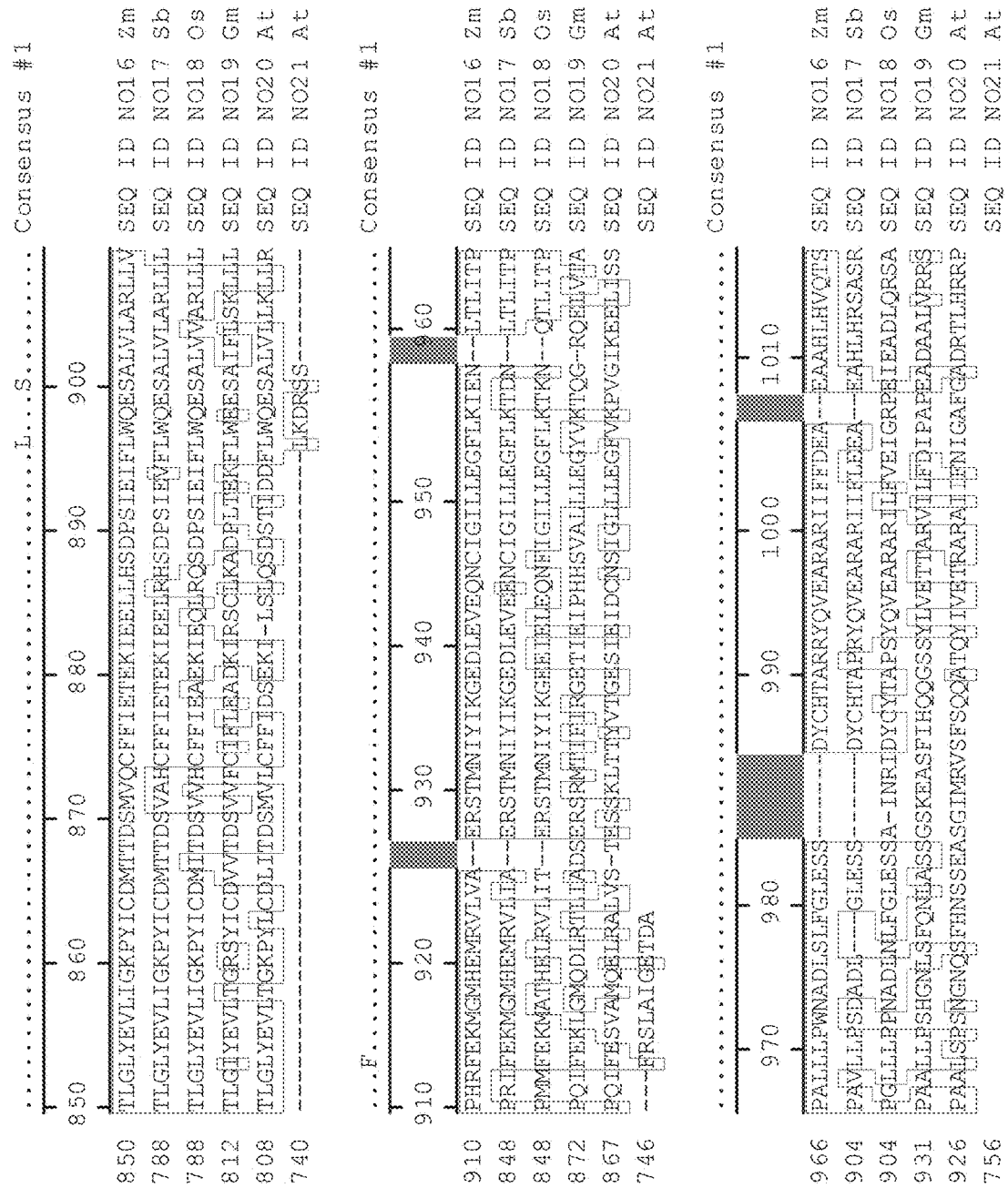

FIGS. 1A-1H show the multiple alignment of the amino acid sequences of the antiporter/sodium ion transporter polypeptides of SEQ ID NOs:16, 17, 18, 19, 20, and 21. Residues that are identical to the residue of SEQ ID NO:16 at a given position are enclosed in a box. A consensus sequence is presented where a residue is shown if identical in all sequences, otherwise, a period is shown.

FIG. 2 shows the percent sequence identity and the divergence values for each pair of amino acids sequences of antiporter/sodium ion transporter polypeptides displayed in FIGS. 1A-1E.

The sequence descriptions and Sequence Listing attached hereto comply with the rules governing nucleotide and/or amino acid sequence disclosures in patent applications as set forth in 37 C.F.R. § 1.821 1.825. The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (2):345 373 (1984) which are herein incorporated by reference. The symbols and format used for nucleotide and amino acid sequence data comply with the rules set forth in 37 C.F.R. § 1.822.

SEQ ID NO:1 is the reference sequence for marker PZE-101127875.

SEQ ID NO:2 is the reference sequence for marker PZE-101136333.

SEQ ID NO:3 is the reference sequence for marker PZE-101137350.

SEQ ID NO:4 is the reference sequence for marker PZE-101138119.

SEQ ID NO:5 is the reference sequence for marker PZE-101138122.

SEQ ID NO:6 is the reference sequence for marker SYN24133.

SEQ ID NO:7 is the reference sequence for marker PZE-101143143.

SEQ ID NO:8 is the reference sequence for marker PZE-101144216.

SEQ ID NO:9 is the reference sequence for marker PZE-101144210.

SEQ ID NO:10 is the reference sequence for marker PZE-101144184.

SEQ ID NO:11 is the reference sequence for marker SYN11646.

SEQ ID NO:12 is the reference sequence for marker SYN11650.

SEQ ID NO:13 is the reference sequence for marker PHM7351.

SEQ ID NO:14 is the reference sequence for marker PHM5908.

SEQ ID NO:15 is the nucleotide sequence of a cDNA that encodes a *Zea mays* antiporter/sodium ion transporter.

SEQ ID NO:16 is the amino acid sequence of the protein encoded by SEQ ID NO:15.

SEQ ID NO:17 is the amino acid sequence of the *Sorghum bicolor* putative uncharacterized protein (Sb08g023290.1).

SEQ ID NO:18 is the amino acid sequence of the *Oryza sativa* putative Na+/H+ antiporter protein (0512g44360.1).

SEQ ID NO:19 is the amino acid sequence of the *Glycine max* SOS1 protein (Glyma08g09730.1).

SEQ ID NO:20 is the amino acid sequence of the *Arabidopsis thaliana* sodium/hydrogen exchanger 7 protein (At2g01980).

SEQ ID NO:21 is the amino acid sequence of the *Arabidopsis thaliana* sodium/hydrogen exchanger 8 protein (At1g14660).

SEQ ID NO:22 is the amino acid sequence of the truncated *Zea mays* antiporter/sodium ion transporter protein that results from the 4 bp deletion in SEQ ID NO:15 at nucleotides 3311-3314.

DETAILED DESCRIPTION

Salt stress is one of the major constraints limiting crop productivity. High salt concentrations in soil restricts water uptake and causes disorder in ion homeostasis. Molecular breeding provides an effective means to improve salinity (salt stress) tolerance in major crops. Through Genome-Wide Association Studies (GWAS) and QTL mapping with bi-parental populations, a major QTL for "early growth vigor" was identified from a collection of Pioneer germplasm. Soil testing and hydroponic culture under high NaCl concentration determined that the observed poor "early growth vigor" phenotype was caused by decreased tolerance to high soil salt concentration, and the QTL identified confers salinity tolerance in maize. Taking the map-based cloning approach, a candidate gene for the QTL has been identified. A deletion in the coding sequence in the susceptible allele of the candidate gene is the likely causative mutation.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "abiotic stress" refers to environmental conditions that reduce growth and yield below optimum levels. Abiotic stress may be at least one condition selected from the group consisting of: drought, water deprivation, flood, high light intensity, high temperature, low temperature, salinity, etiolation, defoliation, heavy metal toxicity, anaerobiosis, nutrient deficiency, nutrient excess, UV irradiation, atmospheric pollution (e.g., ozone) and exposure to chemicals (e.g., paraquat) that induce production of reactive oxygen species (ROS).

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of the trait. The presence of the allele is an indicator of how the trait will be expressed.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence. In maize, a number of BACs each containing a large insert of maize genomic DNA from maize inbred line B73, have been assembled into contigs (overlapping contiguous genetic fragments, or "contiguous DNA"), and this assembly is available publicly on the internet.

A BAC fingerprint is a means of analyzing similarity between several DNA samples based upon the presence or absence of specific restriction sites (restriction sites being nucleotide sequences recognized by enzymes that cut or "restrict" the DNA). Two or more BAC samples are digested with the same set of restriction enzymes and the sizes of the fragments formed are compared, usually using gel separation.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait. Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less.

Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

The term "contiguous DNA" refers to an uninterrupted stretch of genomic DNA represented by partially overlapping pieces or contigs.

When referring to the relationship between two genetic elements, such as a genetic element contributing to abiotic stress tolerance and a proximal marker, "coupling" phase linkage indicates the state where the "favorable" allele at the genetic element contributing to abiotic stress tolerance is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

SHD or DAYSHD=DAYS TO POLLEN SHED: means number of days to 50% of plants shedding pollen.

SLK or DAYSLK=DAYS TO SILKING: means number of days to 50% of plants exposing silks.

"Developmentally regulated promoter" refers to a promoter whose activity is determined by developmental events.

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

EGRWTH=EARLY GROWTH: This trait can be measured as a visual score of early seedling health on a scale of 1 to 9, with 9 as optimal. Another way to evaluate the EGRWTH phenotype is to obtain fresh weight of young plants.

EARHT=EAR HEIGHT: The ear height is a measure from the ground to the highest placed developed ear node attachment and is measured in inches.

An "elite line" is any line that has resulted from breeding and selection for superior agronomic performance.

An "exotic maize strain" or an "exotic maize germplasm" is a strain derived from a maize plant not belonging to an available elite maize line or strain of germ plasm. In the context of a cross between two maize plants or strains of germ plasm, an exotic germ plasm is not closely related by descent to the elite germplasm with which it is crossed. Most commonly, the exotic germplasm is not derived from any known elite line of maize, but rather is selected to introduce novel genetic elements (typically novel alleles) into a breeding program.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

A "favorable allele" is the allele at a particular locus that confers, or contributes to, an agronomically desirable phenotype, e.g., increased tolerance to salt stress, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

"Heterologous" with respect to sequence means a sequence that originates from a foreign species, or, if from the same species, is substantially modified from its native form in composition and/or genomic locus by deliberate human intervention.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps or physical maps, cleaned date, or the use of new algorithms.

The term "inbred" refers to a line that has been bred for genetic homogeneity.

"Increased stress tolerance" or "increased tolerance to stress" of a plant is measured relative to a reference or control plant, and is a trait of the plant to survive under stress conditions over prolonged periods of time, without exhibiting the same degree of physiological or physical deterioration relative to the reference or control plant grown under similar stress conditions.

A plant with "increased stress tolerance" can exhibit increased tolerance to one or more different stress conditions including but not limited to salt (salinity) stress and drought. Plants with increased stress tolerance may exhibit an increase in yield, greenness, biomass, or other yield-related trait under stress conditions. A yield-related trait may be early growth (EGRWTH), days to pollen shed (SHD), days to silking (SLK), plant height (PLTHT), or ear height (EARHT).

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

"Maize" refers to a plant of the *Zea mays* L. ssp. *mays* and is also known as "corn".

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

PLTHT=PLANT HEIGHT: This is a measure of the height of the plant from the ground to the tip of the tassel in inches.

A maize plant "derived from an inbred in the Stiff Stalk Synthetic population" may be a hybrid.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hi-Bred Marker', followed by a number that is specific to the sequence from which it was designed, followed by a "." or a "−" and then a suffix that is specific to the DNA polymorphism. A marker version can also follow (A, B, C etc.) that denotes the version of the marker designed to that specific polymorphism.

The term "progeny" refers to the offspring generated from a cross.

A "progeny plant" is a plant generated from a cross between two plants.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the term "salt stress" refers to high salinity soil conditions that cause damage to plant function or development, whether that damage is reversible or irreversible. In some instances, 4.0 dS/m is used as a general threshold electrical conductivity to define saline soils; however, some crops may show symptoms and reduced yields at electrical conductivities of 2-4 dS/m. As used herein, salt stress may occur when electrical conductivity of the soil is at least about 2 dS/m, 3 dS/m, 4 dS/m, 5 dS/m, 6 dS/m, 7 dS/m, 8 dS/m, 9 dS/m, or 10 dS/m. Alternatively, salt stress can be evaluated using NaCl concentration in the soil. As such, salt stress may occur when NaCl concentration in the soil is at least about 20 mM, 30 mM, 40 mM, 50 mM, 60 mM, 70 mM, 80 mM, 90 mM, or 100 mM.

A "topcross test" is a test performed by crossing each individual (e.g. a selection, inbred line, clone or progeny individual) with the same pollen parent or "tester", usually a homozygous line.

"Tissue-specific promoter" and "tissue-preferred promoter" are used interchangeably, and refer to a promoter that is expressed predominantly but not necessarily exclusively in one tissue or organ, but that may also be expressed in one specific cell.

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct. "Transgenic plant" also includes reference to plants which comprise more than one heterologous polynucleotide within their genome. Each heterologous polynucleotide may confer a different trait to the transgenic plant.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% A SDS, incubating at 65° C., with wash in 0.2×SSC, and 0.1% A SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the CLUSTAL V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the CLUSTAL V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the CLUSTAL V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Genetic Mapping

It has been recognized for quite some time that specific genetic loci correlating with particular phenotypes, such as salt and/or drought tolerance, can be mapped in an organism's genome. Mapping can identify molecular markers that can be advantageously used to identify desired individuals by detecting marker alleles that show a statistically significant probability of co-segregation with a desired phenotype, manifested as linkage disequilibrium. Mapping can also be used to identify the causal gene and/or causal variations in the gene that lead to a specific phenotype.

A variety of methods well known in the art are available for detecting molecular markers or clusters of molecular markers that co-segregate with a trait of interest, such as salt tolerance and/or drought tolerance. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis and 2) Traditional linkage analysis.

In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Maize marker loci that demonstrate statistically significant co-segregation with tolerance to salt stress and/or drought, as determined by traditional linkage analysis and by whole genome association analysis, are provided herein. Detection of these loci or additional linked loci can be used in marker assisted maize breeding programs to produce plants having increased tolerance to salt stress and/or drought and to counter select maize plants that have decreased tolerance to salt stress and/or drought. Activities in marker assisted maize breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germ plasm improvement activities based on presence of favorable nucleic acid sequences.

QTL

A QTL on chromosome 1, bin 6, was identified as being associated with yield under abiotic stress conditions such as salt and/or drought stress (Example 1). The QTL is located at 142.6-156.0 cM on an internally derived proprietary single meiosis based genetic. The QTL was validated using traditional QTL mapping in doubled haploid breeding populations (Example 2) and by marker assisted selection (Example 3). The QTL was found to be associated with early growth (EGRWTH), days to pollen shed (SHD), days to silking (SLK), plant height (PLTHT), and ear height (EARHT) under salt stress conditions. The QTL was also found to be associated with drought tolerance (Example 6).

Chromosomal Intervals

Chromosomal intervals that correlate with tolerance or improved tolerance to one or more abiotic stress such as salt and drought stress are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for abiotic stress tolerance. Table 2 shows markers within the chromosome 1 QTL region that were shown herein to associate with salt stress tolerance. Reference sequences for each of the markers are represented by SEQ ID NOs: 1-12.

Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The intervals described below encompass markers that co-segregate with salt stress tolerance. The clustering of markers that co-segregate with salt stress tolerance within a localized region occurs in relatively small domains on the chromosomes, indicating the presence of one or more QTL in those chromosome regions. The interval was drawn to encompass markers that co-segregate with salt stress tolerance. The intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown.

The chromosome 1 interval may encompass any of the markers identified herein as being associated with the salt stress tolerance trait including: PZE-101127875, PZE-101136333, PZE-101137350, PZE-101138119, PZE-101138122, SYN24133, PZE-101143143, PZE-101144216, PZE-101144210, PZE-101144184, SYN11646, SYN11650, PHM7351, and PHM5908. The chromosome 1 interval, for example, may be bounded by markers PZE-101127875 and SYN11650 (Example 1) or markers PHM7351 and PHM5908 (Example 2). Any marker located within these intervals can find use as a marker for salt stress tolerance and/or drought tolerance and can be used in the context of the methods presented herein to identify and/or select maize plants that have increased tolerance to salt stress and/or increased tolerance to drought stress.

Chromosomal intervals can also be defined by markers that are linked to (show linkage disequilibrium with) a QTL marker and $r^2$ is a common measure of linkage disequilibrium (LD) in the context of association studies. If the $r^2$ value of LD between a chromosome 1 marker locus located at or near the QTL associated with salt tolerance, for example, and another chromosome 1 marker locus in close proximity is greater than ⅓ (Ardlie et al., Nature Reviews Genetics 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1V0 chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with salt stress tolerance and/or drought tolerance, it is important to note that the marker locus is not necessarily responsible for the expression of the salt tolerance phenotype. For example, it is not a requirement that the marker polynucleotide sequence be part of a gene that is responsible for the phenotype (for example, is part of the gene open reading frame). The association between a specific marker allele and a trait is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the parent having the favorable trait that is used to create segregating populations. This does not change the fact that the marker can be used to monitor segregation of the phenotype. It only changes which marker allele is considered favorable in a given segregating population.

Methods presented herein include detecting the presence of one or more marker alleles associated with increased tolerance to salt stress and/or drought in a maize plant and then identifying and/or selecting maize plants that have favorable alleles at those marker loci or detecting the presence of a marker allele associated with decreased tolerance to salt stress and then identifying and/or counter selecting maize plants that have unfavorable alleles (e.g. Haplotype "A"). Markers listed in Tables 2 and 3 have been identified herein as being associated with tolerance to salt stress and hence can be used to predict tolerance to salt stress and/or drought in a maize plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map; IBM2 distance is on average 2.5-3× the distance due to the high resolution nature of this map) of any of the markers in Tables 2 and 3 could also be used to predict tolerance to salt stress and/or drought tolerance in a maize plant.

An unfavorable QTL allele was detected in a maize plant, wherein the unfavorable QTL allele is associated with decreased tolerance to salt stress and/or drought and comprises a 4 bp deletion in the *Zea mays* antiporter/sodium ion transporter gene at nucleotides 3311-3314 of SEQ ID NO:15. Thus, the methods herein involve detecting the presence or absence of the QTL allele wherein a maize plant identified as having the unfavorable QTL allele can be counter selected or removed from a breeding program while a maize plant identified as having favorable QTL allele can be selected and introgressed into other maize plants through the process of marker assisted selection.

Marker Assisted Selection

Molecular markers can be used in a variety of plant breeding applications (e.g. see Staub et al. (1996) *Hortscience* 31: 729-741; Tanksley (1983) *Plant Molecular Biology Reporter*. 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. Any type of marker, either alone or in combination with other markers due to linkage disequilibrium (i.e. a haplotype), can be used in marker assisted selection protocols including but not limited to SNPs, SSRs, expressed sequence tags (ESTs), SSR markers derived from EST sequences, randomly amplified polymorphic DNA (RAPD), and other nucleic acid based markers.

The skilled artisan would expect that there might be additional polymorphic sites at marker loci in and around the chromosome 1 markers identified herein, wherein one or more polymorphic sites is in linkage disequilibrium (LD) with an allele at one or more of the polymorphic sites in the haplotype and thus could be used in a marker assisted selection program to introgress a QTL allele of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the salt stress tolerance QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

Plant Compositions

Maize plants identified and/or selected by any of the methods described above are also of interest.

Gene Identification

The *Zea mays* antiporter/sodium ion transporter gene (SEQ ID NO:15) is located at 151.3 cM on the internal proprietary single meiosis based genetic map. Intracellular Na+/H+ antiporters play important roles in maintaining homeostasis of Na+ and K+. In plants, NHXs direct the movement of Na+ or K+ across the tonoplast and into the vacuole (or other organelles) by catalyzing the exchange of Na+ and/or K+ for H+(Eckardt and Berkowitz. 2011. *Plant Cell* 23:3087-3088). The polypeptide encoded by the *Zea mays* antiporter/sodium ion transporter (i.e. SEQ ID NO:16) is orthologous to AtSOS1/ATNHX7 (SEQ ID NO:20) as well as polypeptides from *Sorghum bicolor* (SEQ ID NO:17), *Oryza sativa* (SEQ ID NO:18), *Glycine max* (SEQ ID NO:19), and *Arabidopsis thaliana* (SEQ ID NO:21).

Methods of Identifying Variants with Effects on the Abiotic Stress Tolerance Phenotype Methods of identifying variants of an antiporter/sodium ion transporter gene that give plants increased tolerance to salt stress is also provided. Such methods may comprise: (a) combining through gene shuffling one or more nucleotide sequences encoding one or more fragments of SEQ ID NO:16, 17, 18, 19, 20, or 21 or a protein that is at least 80%, 85%, 90%, 95%, or 100% identical to SEQ ID NO:16, 17, 18, 19, 20, or 21, or a fragment thereof; (b) transforming the shuffled sequences from step (a) into a population of regenerable plant cells; (c) regenerating a population of transformed plants from the population of transformed regenerable plant cells of step (b); (d) screening the population of transformed plants from step (c) for increased tolerance to salt stress and/or drought; and (e) identifying the variant from the transformed plant exhibiting the increased tolerance to salt stress and/or drought. The method can further comprise: (f) introducing into a regenerable plant cell a recombinant construct comprising a variant of an antiporter/sodium ion transporter gene described herein that gives plants increased tolerance to salt stress and/or drought; (g) regenerating a transgenic plant from the regenerable plant cell after step (f), wherein the transgenic plant comprises in its genome the recombinant DNA construct; and (h) selecting a transgenic plant of (g), wherein the transgenic plant comprises the recombinant DNA construct and exhibits increased tolerance to salt stress and/or drought, when compared to a control plant not comprising the recombinant DNA construct.

The terms "gene shuffling" and "directed evolution" can be used interchangeably herein. The method of "gene shuffling" consists of iterations of DNA shuffling followed by appropriate screening and/or selection to generate variants of crw1 nucleic acids or portions thereof having a modified biological activity (Castle et al., (2004) Science 304(5674): 1151-4; U.S. Pat. Nos. 5,811,238 and 6,395,547).

Methods of identifying allelic variants of the *Zea mays* antiporter/sodium ion transporter gene in maize that are associated with increased tolerance to salt stress and/or drought by way of traditional linkage mapping are also provided. In some embodiments, the allelic variants are identified by (a) crossing two maize plants with differing levels of tolerance to salt stress and/or drought; (b) evaluating allelic variations in the progeny plants with respect to the polynucleotide sequence encoding a protein comprising SEQ ID NO:16, 17, 18, 19, 20, or 21, or in the genomic region that regulates the expression of the polynucleotide encoding the protein; (c) phenotyping the progeny plants for tolerance to salt stress and/or drought; (d) associating allelic variations with said tolerance to salt stress and/or drought; and (e) identifying the alleles that are associated with increased tolerance to salt stress and/or drought. The phenotyping step (c) could be performed using any method known in the art.

In other embodiments the allelic variants are identified through whole genome association analysis by: (a) obtaining a population of maize plants, wherein said maize plants exhibit differing levels of tolerance to salt stress and/or drought; (b) evaluating allelic variations with respect to the polynucleotide sequence encoding a protein comprising SEQ ID NO:16, 17, 18, 19, 20, or 21, or in the genomic region that regulates the expression of the polynucleotide encoding the protein; (c) associating allelic variations with tolerance to salt stress and/or drought; and (d) identifying an allelic variant that is associated with increased tolerance to salt stress and/or drought.

Also provided are methods of identifying a maize plant that exhibits increased tolerance to salt stress, the method comprising: (a) detecting the presence of at least one allelic variant of the *Zea mays* antiporter/sodium ion transporter gene that is associated with increased tolerance to salt stress and/or drought, in the genome of the maize plant; and (b) identifying a maize plant that comprises said at least one allelic variant. The method can further comprise: (c) crossing said maize plant to a second maize plant; and (d) identifying and selecting progeny plants arising from said cross that have said allelic variant.

Introducing Allelic Variants into Target Site in the Maize Genome

The methods described above may further include introducing the identified variants into a target site in the genome of a plant cell via genome editing, wherein the plant may be maize.

The variants may be introduced using proteins that can introduce DNA damage into preselected regions of the plant genome. Such proteins or catalytic domains are sometimes referred to as "DNA mutator enzymes". The DNA damage can lead to a DSB (double strand break) in double stranded DNA). The DNA mutator enzyme domain may be fused to a protein that binds to specific DNA sites.

Examples of DNA mutator enzyme domains include, but are not limited to catalytic domains such as DNA glycolases, DNA recombinase, transposase, and DNA nucleases (PCT publication No. WO2014127287; US Patent Publication No. US20140087426; incorporated herein by reference).

DNA glycolases are a family of enzymes involved in base excision repair, the mechanism by which damaged bases in DNA are removed and replaced. DNA glycolases include, but are not limited to, 3-methyladenine glycosylase (Magi p) and uracil DNA glycolases.

DNA nuclease domains are another type of enzymes that can be used to introduce DNA damage or mutation. A DNA nuclease domain is an enzymatically active protein or fragment thereof that causes DNA cleavage resulting in a DSB.

DNA nucleases and other mutation enzyme domains may be fused with DNA binding domains to produce the DSBs in the target DNA. DNA binding domains include, for example, an array specific DNA binding domain or a site-specific DNA binding domain. Site specific DNA binding domain include but are not limited to a TAL (Transcription Activator-Like Effector) or a zinc finger binding domain.

Examples of DNA-binding domains fused to DNA nucleases include but are not limited to TALEN and multiple TALENs. Transcription Activator-Like Effector Nucleases (TALENs) are artificial restriction enzymes generated by fusing the TAL effector DNA binding domain to a DNA enzyme domain. TAL proteins are produced by bacteria and include a highly conserved 33-34 amino acid DNA binding domain sequence (PCT publication No. WO2014127287; US Patent Publication No. US20140087426).

The original TALEN chimera were prepared using the wild-type FokI endonuclease domain. However, TALEN may also include chimera made from Fok1 endonuclease domain variants with mutations designed to improve cleavage specificity and cleavage activity. In some instances multiple TALENs can be expressed to target multiple genomic regions.

A zinc finger is another type of DNA binding domain that can be used for introducing mutations into the target DNA.

Various protein engineering techniques can be used to alter the DNA-binding specificity of zinc fingers and tandem repeats of such engineered zinc fingers can be used to target desired genomic DNA sequences.

The proteins of the CRISPR (clustered regularly interspaced short palindromic repeat) system are examples of other DNA-binding and DNA-nuclease domains. The bacterial CRISPR/Cas system involves the targeting of DNA with a short, complementary single stranded RNA (CRISPR RNA or crRNA) that localizes the Cas9 nuclease to the target DNA sequence (Burgess D J (2013) Nat Rev Genet 14:80; PCT publication No. WO2014/127287). The crRNA can bind on either strand of DNA and the Cas9 will cleave the DNA making a DSB.

Cas gene relates to a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. Provisional Application No. 62/023,239, filed Jul. 11, 2014). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can be Cas9 endonuclease, or a functional fragment thereof, such as but not limited to, Cas9 genes listed in SEQ ID NOs: 462, 474, 489, 494, 499, 505, and 518 of WO2007/025097 published Mar. 1, 2007. The Cas endonuclease gene can be a plant, maize or soybean optimized Cas9 endonuclease, such as but not limited to a plant codon optimized *Streptococcus pyogenes* Cas9 gene that can recognize any genomic sequence of the form N(12-30)NGG. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotride that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The unique properties of meganucleases, namely the property of having very long recognition sequences (>14 bp) making them highly specific, can be exploited to make site-specific DSB in genome editing; however, not enough meganucleases are known, or may ever be known, to cover all possible target sequences. Meganuclease variants can be created to recognize specific sequences; however, the construction of sequence specific enzymes for all possible sequences is costly and time consuming.

Transgenic Plants and Methods of Increasing Tolerance to Salt Stress and/or Drought in a Plant Preferred haplotypes and QTL identified by the present disclosure may be advanced as candidate genes for inclusion in expression constructs, i.e., transgenes. Nucleic acids underlying haplotypes or QTL of interest may be expressed in plant cells by operably linking them to a promoter functional in plants. Methods are known in the art for assembling and introducing constructs into a cell in such a manner that the nucleic acid molecule for a trait is transcribed into a functional mRNA molecule that is translated and expressed as a protein product.

As such, provided herein are recombinant DNA constructs comprising a polynucleotide operably linked to at least one regulatory sequence wherein said polynucleotide comprises a nucleic acid sequence encoding an amino acid sequence of at least 80%, 85%, 90%, 95% or 100% sequence identity, based on the Clustal V method of alignment, when compared to SEQ ID NO:16, 17, 18, 19, 20, or 21, is also provided. The regulatory sequence may be any promoter functional in a plant cell. Also provided are transgenic plant cells, plants, and seeds containing the recombinant DNA constructs. The plant may be *Arabidopsis*, maize, soybean, sunflower, sorghum, canola, wheat, alfalfa, cotton, rice, barley, millet, sugar cane, or switchgrass.

The recombinant DNA constructs may be used to increase tolerance to salt stress and/or drought in a plant by introducing a recombinant DNA construct disclosed herein into a regenerable plant cell and regenerating a transgenic plant. Progeny plants may also be obtained from the transgenic plants.

Stacking

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

Seed Treatments

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluquinconazole, flurazole, fluxofenim, harpin protein, imazalil, imidacloprid, ipconazole, isoflavenoids, lipochitooligosaccharide, mancozeb, manganese, maneb, mefenoxam, metalaxyl, metconazole, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seeds that produce plants with specific traits (such as tolerance to abiotic stress such as salt and drought) may be tested to determine which seed treatment options and application rates may complement such plants in order to enhance yield. For example, a plant with good yield potential but head smut susceptibility may benefit from the use of a seed treatment that provides protection against head smut, a plant with good yield potential but cyst nematode susceptibility may benefit from the use of a seed treatment that provides protection against cyst nematode, and so on. Further, the good root establishment and early emergence that results from the proper use of a seed treatment may result in more efficient nitrogen use, a better ability to withstand drought and an overall increase in yield potential of a plant or plants containing a certain trait when combined with a seed treatment.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Association Mapping Analysis

One hundred and ten elite non-stiff stalk (NSS) lines were grown in the high soil salinity location in Location 1 and were scored on a per row basis for seedling vigor, also called early growth (EGRWTH). The lines were genotyped at 56,000 SNP markers across the maize genome. Genome wide association mapping was then performed to identify markers associated with the early growth (EGRWTH) phenotype in Location 1. Phenotypic and genotypic scores from all tested individuals were input into each association analysis The most significant peak for the early growth phenotype was identified on chromosome 1 in a region from 142.6-156.0 cM on a single meiosis based genetic map. One haplotype within this region, herein referred to as haplotype "A", associated with lower early growth, with an average score of 3.8 on a 1 to 9 scale, with 9 as optimal. The average score of all other haplotypes was between 6 and 6.6. Haplotype "A" was the only salt-susceptible (unfavorable) haplotype present in the test set, and 45% of the lines in the test set possessed haplotype "A". Table 1 shows the average scores of haplotypes represented in the set of 110 non-stiff stalk inbreds that were grown in Location 1. Table 2 provides maize markers that demonstrated linkage disequilibrium with the salt tolerant phenotype using the association mapping method. The estimated IBM2 genetic map positions were determined by the IBM2 map positions of other markers on the B73 BAC on which the particular SNP was located.

TABLE 1

Average EGRWTH scores for each haplotype

| Haplotype | Avg EGRWTH | N= |
|---|---|---|
| A | 3.8 | 50 |
| B | 6.5 | 24 |
| C | 6.2 | 20 |
| D | 6.0 | 5 |
| E | 6.5 | 2 |
| F | 6.0 | 2 |
| Misc | 6.6 | 7 |

TABLE 2

Maize markers significantly associated with salt tolerance

| Marker | Reference sequence | P-value | Single meiosis based Genetic Map Position (cM) | Estimated IBM2 Genetic Map Position (cM) |
|---|---|---|---|---|
| PZE-101127875 | SEQ ID NO: 1 | 3.78E−15 | 142.6 | 463.9 |
| PZE-101136333 | SEQ ID NO: 2 | 2.22E−16 | 146.7 | N/A |
| PZE-101137350 | SEQ ID NO: 3 | 2.22E−16 | 147.6 | 486.0 |
| PZE-101138119 | SEQ ID NO: 4 | 2.22E−16 | 149.4 | 508.2 |
| PZE-101138122 | SEQ ID NO: 5 | 2.22E−16 | 149.4 | 508.2 |
| SYN24133 | SEQ ID NO: 6 | 2.22E−15 | 149.9 | 504.8 |
| PZE-101143143 | SEQ ID NO: 7 | 7.11E−15 | 154.2 | N/A |
| PZE-101144216 | SEQ ID NO: 8 | 3.11E−15 | 155.8 | N/A |
| PZE-101144210 | SEQ ID NO: 9 | 5.55E−15 | 155.8 | N/A |
| PZE-101144184 | SEQ NQ: 10 | 5.55E−15 | 155.9 | N/A |
| SYN11646 | SEQ ID NO: 11 | 4.22E−15 | 155.9 | N/A |
| SYN11650 | SEQ ID NO: 12 | 2.22E−15 | 156.0 | N/A |

The statistical probabilities that the marker allele and phenotype are segregating independently are reflected in the association mapping probability values (p-values) in Table 2, which is a probability (P) derived from analysis of association between genotype and phenotype. The lower the probability value, the more significant is the association between the marker genotype at that locus and the level of tolerance to salt stress condition.

Example 2

QTL Mapping Using Doubled Haploid Breeding Populations

A biparental mapping population was created by crossing two elite non-stiff stock inbreds, referred to herein as Inbred A and Inbred B, which were contrasting for the salt-tolerance phenotype. 179 doubled haploid lines were generated from the F₁ individuals of this cross. The doubled haploid population was grown in Location 1 in a field with high levels of soil salinity. Vegetative and flowering trait data were collected on the population, including seedling vigor, also known as early growth (EGRWTH), days to pollen shed (SHD), days to silking (SLK), plant height (PLTHT), and ear height (EARHT). The EGRWTH trait is a visual score of early seedling health on a scale of 1 to 9, with 9 as optimal. QTL mapping was performed using composite interval mapping in WinQTLCartographer, and a strong QTL at chromosome 1 from 145.1 cM to 169.6 cM (on the internally derived single meiosis based genetic map) was observed for all five agronomic traits. The QTL was bounded by and included PHM7351-8 and PHM5908-10 (See Table 3 for marker information). The EGRWTH, SHD, SLK, PLTHT, and EARHT traits had LOD scores of 44, 23, 29, 29, and 34, respectively. At this QTL on chromosome 1, Inbred B contained the salt-susceptible haplotype and the stress effect within the population was EGRWTH (−3.2 score), DAYSHD (+6.8 day), DAYSLK (+9 day), PLTHT (−17.6 inch), EARHT (−12.3 inch). Shorter plants and delayed flowering phenotypes are consistent with common responses to environmental stress conditions.

TABLE 3

Marker information for PHM7351-8 and PHM5908-10

| SNP | Marker Name | SNP Position in Marker Reference Sequence | Single meiosis based genetic map position (cM) | IBM2 Genetic Map Position (cM) |
|---|---|---|---|---|
| PHM7351-8 | PHM7351 | 138 in SEQ ID NO: 13 | 145.1 | 485.9 |
| PHM5908-10 | PHM5908 | 148 in SEQ ID NO: 14 | 169.6 | 593.8 |

Three additional double haploid populations were evaluated at both a high soil salinity location (Location 1) and at an average soil salinity location (Location 2). The double haploid populations were created by crossing elite non-stiff stock inbreds to a tester line, and then using the resulting F₁ individuals to generate double haploid populations with population sizes of 149, 174, and 40, respectively. The elite non-stiff stock inbreds all contained the salt susceptible haplotype at the chromosome 1 QTL, which was associated with shorter plants and delayed flowering in Location 1 but had a negligible effect in Location 2 (Table 4).

TABLE 4

Effect of QTL1 in three doubled haploid populations at high soil salinity (Location 1) and average soil salinity levels (Location 2).

| | Population 1 (N = 149) | | Population 2 (N = 174) | | Population 3 (N = 40) | |
|---|---|---|---|---|---|---|
| | Location 1 | Location 2 | Location 1 | Location 2 | Location 1 | Location 2 |
| EARHT (in) | −8.9 | −0.7 | −6.3 | −2 | −5 | −0.6 |
| PLTHT (in) | −14.7 | −0.9 | −10.6 | −1.2 | −14 | −3.4 |
| SHD (days) | 6.8 | 0.4 | 6.8 | 1.5 | 5.3 | 0.2 |
| SLK (days) | 7.3 | 0.2 | 7.1 | 1.1 | 5.4 | 0.2 |

Example 3

Early Growth Phenotype Caused by Differential Salinity Tolerance

A hydroponic study using a selection of inbreds from the test set used in EXAMPLE 1 was performed to validate a surrogate assay in a controlled environment to be used for map based gene cloning of the chromosome 1 QTL. Nine inbreds with varying responses to soil salinity in Location 1 were selected for testing in hydroponic high saline conditions. Ten plants of each inbred were grown for four weeks at normal conditions and in 100 mM NaCl conditions. After four weeks, the plants were scored on a 1 to 9 scale, with 9 as the healthiest and largest plants and 1 as the smallest or dead plants. The ten plants of each inbred were averaged to give a single score (Table 5). There was a strong correlation between inbred response to high soil salinity conditions in Location 1 and response to 100 mM salt conditions in the hydroponics study. Inbreds with Haplotype A showed considerably less seedling vigor in both high salt soils and 100 mM salt conditions in the hydroponics study.

TABLE 5

Comparison of inbred lines under high salt field conditions and high salt hydroponic conditions

| Inbred | Haplotype | EGRWTH in Location 1 | 100 mM salt in Hydroponics |
|---|---|---|---|
| Inbred C | A | 2 | 2.6 |
| Inbred D | A | 2 | 1 |
| Inbred E | A | 3 | 2.3 |
| Inbred F | A | 4 | 1 |
| Inbred G | A | 4 | 1 |
| Inbred H | D | 7 | 8.1 |
| Inbred I | C | 7 | 4.6 |
| Inbred J | B | 8 | 6.6 |
| Inbred A | B | 8 | 7.9 |

Example 4

Effect of QTL in Hybrid Combinations

Yield data from a segregating population indicates that the QTL has an impact on hybrid yield under high salinity soil conditions. The 179 double haploid lines of the Inbred A X Inbred B population were toperossed to a stiff-stock tester to be used in yield test trials. The toperossed population was grown in two high salt locations (referred to herein as Locations 3 and 4). At both locations, hybrid lines with the salt-tolerant haplotype showed higher ear height and plant height; moreover, hybrid lines with the salt-tolerant haplotype showed yield increases of 5.3 bu/a and 4.0 bu/a for locations 3 and 4, respectively (Table 6).

TABLE 6

Effect of QTL1 in a yield test experiment

| Location | Trait | Avg of lines with HapA | Avg of lines with HapB | Difference between haplotypes |
|---|---|---|---|---|
| Location 3 | EARHT (in) | 40.1 | 41.8 | 1.7 |
| Location 3 | PLTHT (in) | 116.8 | 118.9 | 2.2 |
| Location 3 | YIELD (bu/a) | 111.2 | 116.4 | 5.3 |
| Location 4 | EARHT (in) | 46.3 | 48 | 1.7 |
| Location 4 | PLTHT (in) | 122.5 | 124.4 | 1.9 |
| Location 4 | YIELD (bu/a) | 73.8 | 77.8 | 4 |

Example 5

Cloning of the Gene Conferring Salinity Tolerance

A map based cloning approach was used to identify and clone the gene responsible for salinity tolerance. First, 350 pre-existing doubled haploid populations with contrasting haplotypes at the QTL were identified. Twenty four large doubled haploid populations, consisting of 4130 doubled haploid lines, were used for fine mapping and cloning. Molecular markers were used to identify double haploid lines with recombination events within the QTL interval, and selected recombinant plants were chosen for phenotyping (using hydroponic evaluation) and genotyping. Ten plants of each line, along with inbred parent controls were grown for 4 weeks in both normal conditions and 100 mM saline solution. After five rounds of consecutive hydroponic phenotyping and genotyping, the QTL region was further delimited to a region of chromosome 1 from 150.96-151.93 cM on a single meiosis genetic map.

Analysis of 68 SNPs in a region from 150-151.6 revealed that haplotypes A and B (see Example 1; Table 1) appeared to have arisen from a common ancestor. However, lines with haplotype "B" were salt-tolerant, while lines with haplotype "A" were salt-susceptible.

Further analysis of this region identified a gene encoding an antiporter/sodium ion transporter (SEQ ID NOs:15 and 16 represent the gene and protein sequences, respectively) at 151.27 cM (on a single meiosis genetic map). BLASTP results against the NCBI nr database showed that SEQ ID NO:16 is 99.9% similar to a Zea mays hypothetical protein (NCBI GI No. 414869179).

Haplotype "A" has a 4 bp deletion in the coding sequence of this gene, at nucleotides 3311-3314 of SEQ ID NO:15, resulting in a frameshift of the coding sequence that changes the last 78 amino acids of the protein (the resulting sequence is represented by SEQ ID NO:22). No other identified haplotype possessed this 4-bp deletion.

Example 6

Effects of QTL1 on Drought Tolerance

A hydroponics pilot study was performed to assess drought tolerance of lines containing the unfavorable Haplotype "A" as compared to lines containing a favorable haplotype (e.g. Haplotype "B"). Three pairs of near isogenic lines (NILs) were evaluated for the early growth phenotype, in a per se experiment and in a topeross experiment (in hybrid combination). Significant differences between lines having Haplotype "A" versus lines having Haplotype "B" were observed in two of the three per se NIL experiments. A difference was also observed in the third set of NILs; however, the difference was not statistically significant. Table 7 shows the results of the hydroponics experiments.

TABLE 7

Haplotypes at QTL and their association with drought tolerance

| | Test | Haplotype | Fresh Weight Mean (g) | n (sample size) | p-value (T-test) |
|---|---|---|---|---|---|
| NIL Pair 1 | per se | B | 30 | 8 | 0.0002 |
| | per se | A | 17.1 | 8 | |
| | TC | B | 54.4 | 8 | 0.0091 |
| | TC | A | 36.9 | 8 | |
| NIL Pair 2 | per se | B | 28.7 | 8 | 0.019 |
| | per se | A | 21.1 | 4 | |
| | TC | B | 41.6 | 8 | 0.25 |
| | TC | A | 45 | 8 | |
| NIL Pair 3 | per se | B | 22.7 | 8 | 0.47 |
| | per se | A | 21.7 | 8 | |
| | TC | B | 34.3 | 8 | 0.42 |
| | TC | A | 32.1 | 8 | |

Example 7

Use of Zea mays Antiporter/Sodium Ion Transporter Gene as a Transgene to Create Corn Plants with Increased Salinity and/or Drought Tolerance The Zea mays antiporter/sodium transporter gene described herein can be expressed as a transgene as well, allowing modulation of its expression in different circumstances. The Zea mays antiporter/sodium transporter candidate gene can be expressed using its own promoter; at a low level behind the promoters of either a rice actin gene (U.S. Pat. Nos. 5,641,876 and 5,684,239) or the F3.7 gene (U.S. Pat. No. 5,850,018); throughout the plant at a high level behind the promoter, 5' untranslated region and an intron of a maize ubiquitin gene (Christensen et al. (1989) Plant Mol. Biol. 12:619-632; Christensen et al. (1992) Plant Mol. Biol. 18:675-689); or at a root-preferred, low level behind a root-preferred promoter such as but not limited to, maize NAS2 promoter, the maize Cyclo promoter (US 2006/0156439, published Jul. 13, 2006), the maize ROOTMET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664). A recombinant DNA construct containing the transgene behind the chosen promoter can be transformed into maize as described in Example 8.

Example 8

*Agrobacterium*-Mediated Transformation of Maize and Regeneration of Transgenic Plants Maize can be transformed with selected polynucleotide constructs described in Example 7 using the method of Zhao (U.S. Pat. No. 5,981,840, and PCT patent publication WO98/32326). Briefly, immature embryos can be isolated from maize and the embryos contacted with a suspension of *Agrobacterium*, where the bacteria are capable of transferring the polynucleotide construct to at least one cell of at least one of the immature embryos (step 1: the infection step). In this step the immature embryos is immersed in an *Agrobacterium* suspension for the initiation of inoculation. The embryos are co-cultured for a time with the *Agrobacterium* (step 2: the co-cultivation step). The immature embryos were cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent, and growing transformed callus is recovered (step 4: the selection step). The callus is then regenerated into plants (step 5: the regeneration step), and calli grown on selective medium are cultured on solid medium to regenerate the plants.

Example 9

Candidate Gene Validation with TUSC Allele

A TUSC line was obtained with a Mu insertion within the first exon of the antiporter candidate gene. A plant hemizygous for the TUSC Mu insertion was crossed to PH1V6N, an inbred with the susceptible 4-bp deletion allele. PH1V6N was shown to be susceptible when grown in the high salinity hydroponic assay. Within this hydroponics salinity assay, an $F_1$ of an inbred with the 4-bp allele and a salt tolerant line shows increased salt tolerance compared to the susceptible inbred.

The F1 progeny of the hemizygous TUSC allele and PH1V6N were tested for salinity susceptibility (i.e. tolerance to salt stress) in a high salinity hydroponics assay. The $F_1$ plants were grown for 16 days in a modified Hoaglands nutrient media with a NaCl concentration of 100 mM, maintained at a constant temperature of 65 C. The 84 $F_1$ plants were genotyped with Mu specific primers to distinguish the plants containing a Mu insertion from the Mu-WT plants. After 16 days, the fresh biomass of each plant was measured in grams. Plants with the Mu insertion were significantly smaller than the plants without the Mu insertion (Table 8). The TUSC Mu allele failed to complement the 4-bp deletion allele, proving they are allelic.

TABLE 8

Complementation test results

| | N | Fresh Weight Mean (g) | StDev | SE |
|---|---|---|---|---|
| 4-bp allele/No Mu insertion | 49 | 9.43 | 2.31 | 0.33 |
| 4-bp allele/Mu Insertion | 35 | 4.11 | 3.26 | 0.55 |

T-Test of difference
P-Value = 0.000

Example 10

Transgenic Validation in *Arabidopsis*

The maize antiporter candidate gene was transgenically validated in *Arabidopsis*, using a mutant line for Atsos1, the *Arabidopsis* gene homologue.

When the mutant Atsos1 plants are grown on MS only plates, the mutants are indistinguishable from wild-type, however, when the Atsos1 plants are grown on MS+100 mM NaCl plates, the plants show a susceptible phenotype. The Atsos1 mutant lines were transformed with the tolerant maize cDNA and susceptible maize cDNA with the 4-bp deletion, and the genes were overexpressed with a 35S promoter. The Atsos1/ZmTolerant-cDNA plants showed a tolerant phenotype, and the Atsos1/ZmSusceptible-cDNA plants showed a susceptible phenotype. The candidate gene is validated in *Arabidopsis* since the maize cDNA with the 4-bp deletion allele fails to complement Atsos1.

Example 11

Effects of QTL in 100 mM NaCl Salinity

A hydroponics pilot study was performed to assess salinity tolerance of lines containing the unfavorable Haplotype "A" as compared to lines containing a favorable haplotype (e.g. Haplotype "B"). Three recurrent parents with the unfavorable haplotype were selected to create NILs (near isogenic lines). Donor lines containing the favorable haplotype were backcrossed for three generations into the recurrent parents. Then the NILs were selfed for two generations to create seed that was homozygous for the favorable haplotype and seed that was homozygous for the unfavorable haplotype. The NILs are $BC_3F_3$ lines. The three pairs of near isogenic lines (NILs) were grown in a modified Hoaglands nutrient media for 7 days and then transferred to a modified Hoaglands nutrient media with a NaCl concentration of 100 mM to grow for an additional 21 days. The fresh biomass of each plant was measured in grams. Significant differences between lines having Haplotype "A" versus lines having Haplotype "B" were observed in all three NIL pairs.

TABLE 9

Haplotypes at QTL and their association with salinity tolerance

| Test | Haplotype | Fresh Weight mean (g) | n (sample size) | p-value (T-test) |
|---|---|---|---|---|
| NIL Pair 1 per se | B | 11.4 | 11 | 0.000 |
| | A | 3.5 | 11 | |
| NIL Pair 2 per se | B | 15.9 | 11 | 0.005 |
| | A | 4.3 | 4 | |
| NIL Pair 3 per se | B | 6.7 | 11 | 0.000 |
| | A | 2.3 | 10 | |

Example 12

Identification of Orthologous Sequences

Orthologous sequences of the *Zea mays* antiporter/sodium ion transporter protein (SEQ ID NO:16; NCBI GI No. 414869179) were identified using BLAST and a molecular phylogenetic analysis. The analysis revealed similarity of the *Zea mays* antiporter/sodium ion transporter protein to polypeptides from *Sorghum bicolor* (Sb08g023290.1; SEQ ID NO:17), *Oryza sativa* (O512g44360.1; SEQ ID NO:18), *Glycine max* (Glyma08g09730.1; SEQ ID NO:19), and *Arabidopsis thaliana* (At2g01980 (SEQ ID NO:20) and At1g14660 (SEQ ID NO:21)). A multiple sequence alignment of these polypeptide sequences with the *Zea mays* antiporter/sodium ion transporter protein (SEQ ID NO:16) is shown in FIGS. 1A-1H. FIG. 2 presents the percent sequence identities and divergence values for each sequence pair presented in FIGS. 1A-1H. FiFigureSequence alignments and percent identity calculations were performed using the Megalign® program of the LASERGENE® bioinformatics computing suite (DNASTAR® Inc., Madison, Wis.). Multiple alignment of the sequences was performed using the Clustal V method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

A polynucleotide sequence encoding any of the orthologous polypeptides may be introduced into a recombinant DNA construct, which then can be used to transform plants using standard techniques known to one of ordinary skill in the art, in order to increase tolerance to salt stress and/or drought in plants.

```
                        SEQUENCE LISTING

<160> NUMBER OF SEQ ID NOS: 23

<210> SEQ ID NO 1
<211> LENGTH: 101
<212> TYPE: DNA
<213> ORGANISM: artificial
<220> FEATURE:
<223> OTHER INFORMATION: Reference sequence for marker

<400> SEQUENCE: 1
gtcgtcgtcg tcatgcatga caaacacaaa ccggaggaga atgatgcgag ttattacagc      60
tactagctag caacagtgat ctaaacgccg ccggtttcat c                        101

<210> SEQ ID NO 2
<211> LENGTH: 101
<212> TYPE: DNA
<213> ORGANISM: artificial
<220> FEATURE:
<223> OTHER INFORMATION: Reference sequence for marker

<400> SEQUENCE: 2
gtgtatagta atgtcgatgt cccggtaaaa cctctcaaaa tattcagagc agaacttagt      60
gccattgtct gatctcaaat attgaccttc ttttctgtct a                        101

<210> SEQ ID NO 3
<211> LENGTH: 101
<212> TYPE: DNA
<213> ORGANISM: artificial
<220> FEATURE:
<223> OTHER INFORMATION: Reference sequence for marker

<400> SEQUENCE: 3
ccaaattaga tccgagtctt ttaaatctgg aacgtagacg agtgatccaa tggccgcagt      60
gacttgccgg ttggatgaaa tataatctaa tcggggttgt t                        101

<210> SEQ ID NO 4
<211> LENGTH: 101
<212> TYPE: DNA
<213> ORGANISM: artificial
<220> FEATURE:
<223> OTHER INFORMATION: Reference sequence for marker

<400> SEQUENCE: 4
ttgtagcaac aatcgaacgc tcagcatgag cccgtttgct ggataataag aaataagata      60
ttagccgcca atatgctgct ctagaagata tgtaaaatac g                        101

<210> SEQ ID NO 5
<211> LENGTH: 101
<212> TYPE: DNA
```

```
<213> ORGANISM: artificial
<220> FEATURE:
<223> OTHER INFORMATION: Reference sequence for marker

<400> SEQUENCE: 5
gctttaactg gactctttac ctattaatca catcacccc agaccagagg accagggcag    60
cagaaaccaa tcattctcag aggtgcaacc attcatacta a                      101

<210> SEQ ID NO 6
<211> LENGTH: 121
<212> TYPE: DNA
<213> ORGANISM: artificial
<220> FEATURE:
<223> OTHER INFORMATION: Reference sequence for marker
<220> FEATURE:
<221> NAME/KEY: misc_feature
<222> LOCATION: (82)..(82)
<223> OTHER INFORMATION: n is a, c, g, or t

<400> SEQUENCE: 6
tagagagcct ctgtgcgggg gtgcccatat tgagcgaacc cttcttgcag agcagcagac    60
aaccatcgcc tgctccctcg tngccttgct cctggacatc cgtgtcgtcg tcggcgaccc   120
c                                                                  121

<210> SEQ ID NO 7
<211> LENGTH: 101
<212> TYPE: DNA
<213> ORGANISM: artificial
<220> FEATURE:
<223> OTHER INFORMATION: Reference sequence for marker

<400> SEQUENCE: 7
aaatcaaaat aacacgcggt gaaaggccgg agaggctccg atccatccat agcacggcag    60
gaaggtttag cgcatagatc tagtcttact tctagaaccc g                      101

<210> SEQ ID NO 8
<211> LENGTH: 101
<212> TYPE: DNA
<213> ORGANISM: artificial
<220> FEATURE:
<223> OTHER INFORMATION: Reference sequence for marker

<400> SEQUENCE: 8
agctgtaagc acaaagccgg caaagcgata cccactggcc ttatggatag ccatattggg    60
cctgataatg ttagtcgctg tgtacatctt ctcgttgtct c                      101

<210> SEQ ID NO 9
<211> LENGTH: 101
<212> TYPE: DNA
<213> ORGANISM: artificial
<220> FEATURE:
<223> OTHER INFORMATION: Reference sequence for marker

<400> SEQUENCE: 9
gttgttatcc attcaattca aagggttaca tgtggtcgag gttccggaca atgtggccaa    60
gaaaatgtct cacgttcata tgtaaacttt gcacacttca t                      101

<210> SEQ ID NO 10
<211> LENGTH: 101
<212> TYPE: DNA
<213> ORGANISM: artificial
<220> FEATURE:
<223> OTHER INFORMATION: Reference sequence for marker
```

<400> SEQUENCE: 10
ccgccgcctc caccgcgcct cggccccgcc accgccctcg gactgtagtt tgagataagc    60 tagcaattt tttaggccag tacgcatcac ttctctgttt t                        101

<210> SEQ ID NO 11
<211> LENGTH: 121
<212> TYPE: DNA
<213> ORGANISM: artificial
<220> FEATURE:
<223> OTHER INFORMATION: Reference sequence for marker
<220> FEATURE:
<221> NAME/KEY: misc_feature
<222> LOCATION: (121)..(121)
<223> OTHER INFORMATION: n is a, c, g, or t

<400> SEQUENCE: 11
gttccccatc gagatgaaga tcctcaacat ggtgaggcac cggaacatcg tcaagatgga    60
agggtactgc atccgcggca acttcggcgt gatcctctcc gagtacatgc cccgaggcac   120 n                                                                  121

<210> SEQ ID NO 12
<211> LENGTH: 121
<212> TYPE: DNA
<213> ORGANISM: artificial
<220> FEATURE:
<223> OTHER INFORMATION: Reference sequence for marker
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 12
ccatttcttt aagcttctgt ttgttttcag tcaaacttga gaataagcgc ggatggagta    60
agctcnataa gtggcaggtt acttctaggt acggccgaag ttatancacc tggtgaactc   120
g                                                                  121

<210> SEQ ID NO 13
<211> LENGTH: 496
<212> TYPE: DNA
<213> ORGANISM: artificial
<220> FEATURE:
<223> OTHER INFORMATION: Reference sequence for marker

<400> SEQUENCE: 13
atatgcgtgt cccccgggga catgagtcaa tggatgtaca tagtcaagct gtcagcggct    60
gagttatcag caaaacatgg agttggtggt tgcttcagga gcctgttggg acagctatta   120
tccgatgttc cagatgttgc tgatgtatct gcgctagcat catggtattg tgaagctgag   180
aactttgatc agcctatcat tgtcataatt gatgatttgg agcaatgttc tggcgatgtg   240
cttggagagt ttgtgatgat gctgagtgag tgggtgttta aaattccagt cttctttgta   300
atggggatag caactaccct tgatgctcca aagaagcttc tctcgtcaga ggctcttcaa   360
cgattagagc cctgcaaact taccttgggg tctccctcag atagattgaa tgcacttgtt   420
gaggctgtcc ttgttaaacc atgcgctgga ttttgcatca gtcatgaagt cgcaatggtc   480
atagctgcct tttcc                                                   496

<210> SEQ ID NO 14
<211> LENGTH: 478
<212> TYPE: DNA
<213> ORGANISM: artificial
<220> FEATURE:
<223> OTHER INFORMATION: Reference sequence for marker

<400> SEQUENCE: 14

```
aagggggaggt cccagtcacg acgttgctca cccttcattt ggtgtttctt tctttctttc    60
tgtctttctt tcaagtcttc aggttcagca agtcaagtta catgcttact tttgaaatca   120
atattcgagg tttcagtctc cggagaactg atacagtgac gatgcattag tgcctgctgc   180
attatttagt ttttttctaca tttttctaca ttctttcttg taacgtgaac tgattcatgt   240
ggatgttctg tgcagccctg aacgaagcgt taaccgccga ggtccaacgt ctgaaactcg   300
cgactgggga ggtaaccgat ggccggatgc cgaagggcct acagcagcag atgaactccc   360
agatgctcca gatccagcag ctgcaggttc agcagcaggc gccccaggca cagcagcagg   420
gccagcgaca gcagcagcag cagcctcaga atcgcataa tcagtaaatt tgggaaaa     478
```

<210> SEQ ID NO 15
<211> LENGTH: 3716
<212> TYPE: DNA
<213> ORGANISM: Zea mays

<400> SEQUENCE: 15

```
tcaaatcagt ttcaactacc taaatactct gttcttcgtc gcttgctctt ccggctcacg    60
gcggtggtct ccggccaagg ggtcgtcaca tacaaggacc agcagagatgg gcggcgaggc  120
tgagcctgac aacgcggtgc tcttcgttgg ggtgtcgctg gtgctgggca tcgcctcccg   180
gcacctcctc cgcggcaccc cgtgccccta caccgtcgcc cttctcgtcc tcggcgtcgc   240
gcttggatcc ctcgagtacg gaacacaaca tggtctaggc aagcttggag ctggaattcg   300
tatctgggct aacataaacc ctgatcttct gctggctgtt tttctacctg ccctcctctt   360
tgaaagctcc ttctccatgg aagtacacca ataaagaga tgtatggcac agatggtgtt   420
acttgctgga cctggtgtgc taatatcaac agttttactt ggcgttgccg taaagctcac   480
ttttccttac aactggagct ggaaaacatc attgttgctt ggcggactgc ttagtgcaac   540
tgatccagtt gctgtggttg cactgctaaa agaactcgga gcaagtaaaa agcttagcac   600
aatcattgaa ggtgaatcct taatgaatga tgggaccgct attgttgcct atcagctatt   660
ctatcgaatg gtgcttggaa gaacctttga tgctggctca ataataaagt tcttgtctga   720
agtttcactt ggagctgttg ctctgggcct tgcatttgga atcatgtcaa tactgtggct   780
gggctttatt tttaacgata caatcataga gattgcactt actcttgctg tcagttatat   840
agctttcttc actgcacaag actcactgga ggtctctggt gttttgactg tcatgacact   900
gggaatgttc tatgcagctt ttgcaaaaac tgcttttaag ggtgaaagtc agcaaagctt   960
acaccatttc tgggaaatgg ttgcttacat tgcaaataca cttatttta tactgagtgg  1020
ggttgttatt gcagatggtg ttctacaaaa taatggccac tttgagaggc acggcagttc  1080
atggggcttc cttcttctgc tctatgtctt tgtacaaata tctcgagtta tagttgttgg  1140
tgttttgtac ccgatgttgc gtcacttttgg gtatgggttg gacttgaaag aggccatgat  1200
tcttgtttgg tcagggctgc gaggggctgt tgctctgtca ctatcattat ctgttaagcg  1260
taccagcgat tcagttcaac cttaccttaa accagaagtt ggaacaatgt ttgtgttctct  1320
cactggtggc attgtgtttc tgacattgat ttttaatggc tcaaccacac aattttttgct  1380
```

```
acatatactc ggcatggaca aattgttgcc cacaaagctt cgtatattga aatatacaag    1440
gtacgaaatg ctaaagaaag cattagaggc ttttggtgaa ctaagggatg acgaggaact    1500
tggacctgct gactgggtta ctgtaaagaa atatatcaca tgtttgaatg acctagacta    1560
tgagccagag catccccatg atgttggtga cgaagatgac tgcatgcata tcatgaactt    1620
aacagatatc cgagtgcggc ttttgaatgg tgtgcaagcc gcgtactggg aatgcttga     1680 agaaggacga ataactcaag ttacagcaaa tattctgatg agatcggttg atgaagctat    1740
ggaccttgtt tctggacaaa cattatgtga ttggaaaggt ttaaagtcca atgtgcagtt    1800
cccaaattac tataggttcc ttcagaggag taggttacca cgaaagcttg tcacatactt    1860
cacagtcgaa agattagagt ctggatgtta catctgtgct gcatttcttc gtgctcacag    1920
aatcgcaagg cggcagctac atgattttct tggtgatagt gaggttgcaa gaactgttat    1980
tgatgaaagt aacgctgagg gggaggaagc tagaaaattc ttggaagatg ttcgagttac    2040
attcccgcag gtgctacgag tgctaaagac acgacaagtc acatattctg tgctgacaca    2100
cttgagtgag tatattcaaa acctccagaa gactgggctg ctggaagaga aggaaatggt    2160
ccatttagat gatgctctgc agacagactt gaagaagttg cagaggaatc accaatagt     2220 gaaaatgcca agagtcagtg atcttctgaa cactcatcct ttagttggcg cgctgcctgc    2280
tgctgtacgt gatactttgc taagcaatac gaaggaaacc ctgcgagggc agggcacaac    2340
gctgtataga gaaggatcca ggccaaccgg tatctggctt gtttctattg gtgtagtgaa    2400
gtggacaagt cagagattaa gcagaaggca ttccttggat ccaatttat cgcatgggag     2460 cactctgggt ctgtatgagg tgctgattgg aaagccatat atctgtgaca tgaccacaga    2520
ttcgatggta cagtgtttct tcatcgaaac tgaaaagata gaagagctgc tccattcaga    2580
tccttcgatt gagattttcc tgtggcagga agtgctctg gtgcttgcca ggcttttggt     2640
ccctcataga ttcgagaaaa tgggaatgca tgagatgagg ttctggttg ctgaaaggtc     2700 gacgatgaac atatacatca agggagaaga cttggaagtg gagcagaatt gcattggcat    2760
tttgctggaa gggttcttga agatcgaaa cctgactctc atcacgcccc cagcgttgct    2820
tctgccatgg aatgctgact tgagcttatt cggtctcgag tcctcagact actgccatac    2880
tgcacgcagg tatcaggtgg aagccagagc gcggatcatc ttcttcgacg aggcagaggc    2940
cgcccatctt catgttcaga caagtgcgtc gctgccccaa ggtgagccag cacggagcat    3000
gagcaaggag cacagcggct tgctcagctg gcccgagagc ttccggaggt ctcgtggcag    3060
cctaggctta gcagctgaga tgctgccggg cggcttgtct tccagggccc tgcaactgag    3120
catgtacggg ggcagcgtgg tgagcctctc ctccggccag cagggtcacc ggcggcagag    3180
gccacgtcat cgcgtgcagg cggccacgac gatgacaaac cagaagaagc acagctcttc    3240
ctaccccagg atgccatcca tatccaagga gcggcatctg ctctccgtgc agtcggaggg    3300
ctccaacatg aagagagtgg cagctctacc tgaggttgct gccaccgctc ctgctccggc    3360
aggggcagca caggggcagc ggagggctat gaacttgcag gaggaataca actcgagcga    3420
agactccgcc ggcgaagaag tcatcgtcag agttgactcg cccagcatgc tctctttccg    3480
tgagtccacc gccgtgcctc cgccccagga gcagtagctg gatgcctgga tgtggtcttc    3540
tcttctcgtg tattgtattg tactgtatgt attgtatcag ggaagctttg gcgcagtggt    3600
gtggtgtggt gtggtgtggt aaacaaaata aataaaacac atttccgcgt tccatatttt    3660
ctcttcatga tcaccgaata aataaaagaa acagagacaa tgatgcggaa gaaaaa         3716
```

<210> SEQ ID NO 16
<211> LENGTH: 1136
<212> TYPE: PRT
<213> ORGANISM: Zea mays

<400> SEQUENCE: 16

```
Met Gly Gly Glu Ala Glu Pro Asp Asn Ala Val Leu Phe Val Gly Val
1               5                   10                  15

Ser Leu Val Leu Gly Ile Ala Ser Arg His Leu Leu Arg Gly Thr Arg
            20                  25                  30

Val Pro Tyr Thr Val Ala Leu Leu Val Leu Gly Val Ala Leu Gly Ser
        35                  40                  45

Leu Glu Tyr Gly Thr Gln His Gly Leu Gly Lys Leu Gly Ala Gly Ile
    50                  55                  60

Arg Ile Trp Ala Asn Ile Asn Pro Asp Leu Leu Leu Ala Val Phe Leu
65                  70                  75                  80

Pro Ala Leu Leu Phe Glu Ser Ser Phe Ser Met Glu Val His Gln Ile
                85                  90                  95

Lys Arg Cys Met Ala Gln Met Val Leu Leu Ala Gly Pro Gly Val Leu
            100                 105                 110

Ile Ser Thr Val Leu Leu Gly Val Ala Val Lys Leu Thr Phe Pro Tyr
        115                 120                 125

Asn Trp Ser Trp Lys Thr Ser Leu Leu Leu Gly Gly Leu Leu Ser Ala
    130                 135                 140

Thr Asp Pro Val Ala Val Val Ala Leu Leu Lys Glu Leu Gly Ala Ser
145                 150                 155                 160

Lys Lys Leu Ser Thr Ile Ile Glu Gly Glu Ser Leu Met Asn Asp Gly
                165                 170                 175

Thr Ala Ile Val Ala Tyr Gln Leu Phe Tyr Arg Met Val Leu Gly Arg
            180                 185                 190

Thr Phe Asp Ala Gly Ser Ile Ile Lys Phe Leu Ser Glu Val Ser Leu
        195                 200                 205

Gly Ala Val Ala Leu Gly Leu Ala Phe Gly Ile Met Ser Ile Leu Trp
    210                 215                 220

Leu Gly Phe Ile Phe Asn Asp Thr Ile Ile Glu Ile Ala Leu Thr Leu
225                 230                 235                 240

Ala Val Ser Tyr Ile Ala Phe Phe Thr Ala Gln Asp Ser Leu Glu Val
                245                 250                 255

Ser Gly Val Leu Thr Val Met Thr Leu Gly Met Phe Tyr Ala Ala Phe
            260                 265                 270

Ala Lys Thr Ala Phe Lys Gly Glu Ser Gln Gln Ser Leu His His Phe
        275                 280                 285

Trp Glu Met Val Ala Tyr Ile Ala Asn Thr Leu Ile Phe Ile Leu Ser
    290                 295                 300

Gly Val Val Ile Ala Asp Gly Val Leu Gln Asn Asn Gly His Phe Glu
305                 310                 315                 320

Arg His Gly Ser Ser Trp Gly Phe Leu Leu Leu Leu Tyr Val Phe Val
                325                 330                 335

Gln Ile Ser Arg Val Ile Val Gly Val Leu Tyr Pro Met Leu Arg
            340                 345                 350

His Phe Gly Tyr Gly Leu Asp Leu Lys Glu Ala Met Ile Leu Val Trp
        355                 360                 365

Ser Gly Leu Arg Gly Ala Val Ala Leu Ser Leu Ser Leu Ser Val Lys
    370                 375                 380
```

-continued

```
Arg Thr Ser Asp Ser Val Gln Pro Tyr Leu Lys Pro Glu Val Gly Thr
385                 390                 395                 400

Met Phe Val Phe Phe Thr Gly Gly Ile Val Phe Leu Thr Leu Ile Phe
            405                 410                 415

Asn Gly Ser Thr Thr Gln Phe Leu Leu His Ile Leu Gly Met Asp Lys
        420                 425                 430

Leu Leu Pro Thr Lys Leu Arg Ile Leu Lys Tyr Thr Arg Tyr Glu Met
    435                 440                 445

Leu Lys Lys Ala Leu Glu Ala Phe Gly Glu Leu Arg Asp Asp Glu Glu
450                 455                 460

Leu Gly Pro Ala Asp Trp Val Thr Val Lys Lys Tyr Ile Thr Cys Leu
465                 470                 475                 480

Asn Asp Leu Asp Tyr Glu Pro Glu His Pro His Asp Val Gly Asp Glu
            485                 490                 495

Asp Asp Cys Met His Ile Met Asn Leu Thr Asp Ile Arg Val Arg Leu
        500                 505                 510

Leu Asn Gly Val Gln Ala Ala Tyr Trp Gly Met Leu Glu Glu Gly Arg
    515                 520                 525

Ile Thr Gln Val Thr Ala Asn Ile Leu Met Arg Ser Val Asp Glu Ala
530                 535                 540

Met Asp Leu Val Ser Gly Gln Thr Leu Cys Asp Trp Lys Gly Leu Lys
545                 550                 555                 560

Ser Asn Val Gln Phe Pro Asn Tyr Tyr Arg Phe Leu Gln Arg Ser Arg
            565                 570                 575

Leu Pro Arg Lys Leu Val Thr Tyr Phe Thr Val Glu Arg Leu Glu Ser
        580                 585                 590

Gly Cys Tyr Ile Cys Ala Ala Phe Leu Arg Ala His Arg Ile Ala Arg
    595                 600                 605

Arg Gln Leu His Asp Phe Leu Gly Asp Ser Glu Val Ala Arg Thr Val
610                 615                 620

Ile Asp Glu Ser Asn Ala Glu Gly Glu Glu Ala Arg Lys Phe Leu Glu
625                 630                 635                 640

Asp Val Arg Val Thr Phe Pro Gln Val Leu Arg Val Leu Lys Thr Arg
            645                 650                 655

Gln Val Thr Tyr Ser Val Leu Thr His Leu Ser Glu Tyr Ile Gln Asn
        660                 665                 670

Leu Gln Lys Thr Gly Leu Leu Glu Glu Lys Glu Met Val His Leu Asp
    675                 680                 685

Asp Ala Leu Gln Thr Asp Leu Lys Lys Leu Gln Arg Asn Pro Pro Ile
690                 695                 700

Val Lys Met Pro Arg Val Ser Asp Leu Leu Asn Thr His Pro Leu Val
705                 710                 715                 720

Gly Ala Leu Pro Ala Val Arg Asp Thr Leu Leu Ser Asn Thr Lys
            725                 730                 735

Glu Thr Leu Arg Gly Gln Gly Thr Thr Leu Tyr Arg Glu Gly Ser Arg
        740                 745                 750

Pro Thr Gly Ile Trp Leu Val Ser Ile Gly Val Val Lys Trp Thr Ser
    755                 760                 765

Gln Arg Leu Ser Arg Arg His Ser Leu Asp Pro Ile Leu Ser His Gly
770                 775                 780

Ser Thr Leu Gly Leu Tyr Glu Val Leu Ile Gly Lys Pro Tyr Ile Cys
785                 790                 795                 800
```

Asp Met Thr Thr Asp Ser Met Val Gln Cys Phe Phe Ile Glu Thr Glu
                805                 810                 815

Lys Ile Glu Glu Leu Leu His Ser Asp Pro Ser Ile Glu Ile Phe Leu
            820                 825                 830

Trp Gln Glu Ser Ala Leu Val Leu Ala Arg Leu Leu Val Pro His Arg
        835                 840                 845

Phe Glu Lys Met Gly Met His Glu Met Arg Val Leu Val Ala Glu Arg
    850                 855                 860

Ser Thr Met Asn Ile Tyr Ile Lys Gly Glu Asp Leu Glu Val Glu Gln
865                 870                 875                 880

Asn Cys Ile Gly Ile Leu Leu Glu Gly Phe Leu Lys Ile Glu Asn Leu
                885                 890                 895

Thr Leu Ile Thr Pro Pro Ala Leu Leu Leu Pro Trp Asn Ala Asp Leu
            900                 905                 910

Ser Leu Phe Gly Leu Glu Ser Ser Asp Tyr Cys His Thr Ala Arg Arg
        915                 920                 925

Tyr Gln Val Glu Ala Arg Ala Arg Ile Ile Phe Asp Glu Ala Glu
    930                 935                 940

Ala Ala His Leu His Val Gln Thr Ser Ala Ser Leu Pro Gln Gly Glu
945                 950                 955                 960

Pro Ala Arg Ser Met Ser Lys Glu His Ser Gly Leu Leu Ser Trp Pro
                965                 970                 975

Glu Ser Phe Arg Arg Ser Arg Gly Ser Leu Gly Leu Ala Ala Glu Met
            980                 985                 990

Leu Pro Gly Gly Leu Ser Ser Arg Ala Leu Gln Leu Ser Met Tyr Gly
        995                 1000                1005

Gly Ser Val Val Ser Leu Ser Ser Gly Gln Gln Gly His Arg Arg
    1010                1015                1020

Gln Arg Pro Arg His Arg Val Gln Ala Ala Thr Thr Met Thr Asn
    1025                1030                1035

Gln Lys Lys His Ser Ser Ser Tyr Pro Arg Met Pro Ser Ile Ser
    1040                1045                1050

Lys Glu Arg His Leu Leu Ser Val Gln Ser Glu Gly Ser Asn Met
    1055                1060                1065

Lys Arg Val Ala Ala Leu Pro Glu Val Ala Ala Thr Ala Pro Ala
    1070                1075                1080

Pro Ala Gly Ala Ala Gln Gly Gln Arg Arg Ala Met Asn Leu Gln
    1085                1090                1095

Glu Glu Tyr Asn Ser Ser Glu Asp Ser Ala Gly Glu Glu Val Ile
    1100                1105                1110

Val Arg Val Asp Ser Pro Ser Met Leu Ser Phe Arg Glu Ser Thr
    1115                1120                1125

Ala Val Pro Pro Pro Gln Glu Gln
    1130                1135

<210> SEQ ID NO 17
<211> LENGTH: 1137
<212> TYPE: PRT
<213> ORGANISM: Sorghum bicolor

<400> SEQUENCE: 17

Met Gly Gly Asp Gly Val Pro Glu Pro Asp Asp Ala Val Leu Phe Val
1               5                   10                  15

Gly Val Ser Leu Val Leu Gly Ile Ala Ser Arg His Leu Leu Arg Gly
            20                  25                  30

-continued

```
Thr Arg Val Pro Tyr Thr Val Ala Leu Leu Val Leu Gly Val Ala Leu
             35                  40                  45
Gly Ser Leu Glu Tyr Gly Thr Gln His Gly Leu Gly Lys Leu Gly Ala
 50                  55                  60
Gly Ile Arg Ile Trp Ala Asn Ile Asn Pro Asp Leu Leu Leu Ala Val
 65                  70                  75                  80
Phe Leu Pro Ala Leu Leu Phe Glu Ser Ser Phe Ser Met Glu Val His
                 85                  90                  95
Gln Ile Lys Arg Cys Met Ala Gln Met Val Leu Leu Ala Gly Pro Gly
                100                 105                 110
Val Val Val Ser Thr Val Leu Leu Gly Ala Ala Val Lys Leu Thr Phe
                115                 120                 125
Pro Tyr Asn Trp Ser Trp Lys Thr Ser Leu Leu Leu Gly Gly Leu Leu
            130                 135                 140
Ser Ala Thr Asp Pro Val Ala Val Ala Leu Leu Lys Glu Leu Gly
145                 150                 155                 160
Ala Ser Lys Lys Leu Ser Thr Ile Ile Glu Gly Glu Ser Leu Met Asn
                165                 170                 175
Asp Gly Thr Ala Ile Val Val Tyr Gln Leu Phe Tyr Arg Met Val Leu
            180                 185                 190
Gly Arg Thr Phe Asp Ala Gly Ser Ile Ile Lys Phe Leu Ser Glu Val
        195                 200                 205
Ser Leu Gly Ala Val Ala Leu Gly Leu Ala Phe Gly Ile Met Ser Ile
    210                 215                 220
Leu Trp Leu Gly Phe Ile Phe Asn Asp Thr Ile Glu Ile Ala Leu
225                 230                 235                 240
Thr Leu Ala Val Ser Tyr Ile Ala Phe Phe Thr Ala Gln Asp Ser Leu
                245                 250                 255
Glu Val Ser Gly Val Leu Thr Val Met Thr Leu Gly Met Phe Tyr Ala
            260                 265                 270
Ala Phe Ala Lys Thr Ala Phe Lys Gly Glu Ser Gln Gln Ser Leu His
        275                 280                 285
His Phe Trp Glu Met Val Ala Tyr Ile Ala Asn Thr Leu Ile Phe Ile
    290                 295                 300
Leu Ser Gly Val Val Ile Ala Asp Gly Val Leu Gln Asn Asn Ala His
305                 310                 315                 320
Phe Glu Arg His Gly Ser Ser Trp Gly Phe Leu Leu Leu Tyr Val
                325                 330                 335
Phe Val Gln Ile Ser Arg Leu Ile Val Val Gly Val Leu Tyr Pro Leu
            340                 345                 350
Leu Arg Gln Phe Gly Tyr Gly Leu Asp Trp Lys Glu Ala Met Ile Leu
        355                 360                 365
Val Trp Ser Gly Leu Arg Gly Ala Val Ala Leu Ser Leu Ser Leu Ser
    370                 375                 380
Val Lys Arg Thr Ser Asp Ala Val Gln Pro Tyr Lys Pro Glu Val
385                 390                 395                 400
Gly Thr Met Phe Val Phe Phe Thr Gly Gly Ile Val Phe Leu Thr Leu
                405                 410                 415
Ile Phe Asn Gly Ser Thr Thr Gln Phe Leu His Met Leu Ser Met
            420                 425                 430
Asp Lys Leu Ser Ala Thr Lys Leu Arg Ile Leu Lys Tyr Thr Arg Tyr
        435                 440                 445
```

```
Glu Met Leu Asn Lys Ala Leu Glu Ser Phe Gly Glu Leu Arg Asp Asp
450                 455                 460
Glu Glu Leu Gly Pro Ala Asp Trp Ile Thr Val Lys Lys Tyr Ile Thr
465                 470                 475                 480
Cys Leu Asn Asp Leu Asp Asn Glu Pro Glu His Pro His Asp Val Ser
                    485                 490                 495
Gly Lys Asp Asp His Met His Ile Met Asn Leu Thr Asp Ile Arg Val
                500                 505                 510
Arg Leu Leu Asn Gly Val Gln Ala Ala Tyr Trp Gly Met Leu Glu Glu
            515                 520                 525
Gly Arg Ile Thr Gln Ala Thr Ala Asn Ile Leu Met Arg Ser Val Asp
530                 535                 540
Glu Ala Met Asp Leu Val Ser Glu Gln Lys Leu Cys Asp Trp Lys Gly
545                 550                 555                 560
Leu Lys Ser Asn Val Gln Phe Pro Asn Tyr Arg Phe Leu Gln Met
                565                 570                 575
Ser Arg Leu Pro Arg Lys Leu Val Thr Tyr Phe Thr Val Glu Arg Leu
            580                 585                 590
Glu Ser Gly Cys Tyr Ile Cys Ala Ala Phe Leu Arg Ala His Arg Ile
        595                 600                 605
Ala Arg Arg Gln Leu His Asp Phe Leu Gly Asp Ser Glu Val Ala Arg
610                 615                 620
Thr Val Ile Asp Glu Ser Asn Ala Glu Gly Glu Glu Ala Arg Lys Phe
625                 630                 635                 640
Leu Glu Asp Val Arg Val Thr Phe Pro Gln Val Leu Arg Val Leu Lys
                645                 650                 655
Thr Arg Gln Val Thr Tyr Ser Val Leu Thr His Leu Ser Glu Tyr Ile
            660                 665                 670
Gln Asn Leu Gln Lys Thr Gly Leu Leu Glu Glu Lys Glu Met Val Gln
        675                 680                 685
Leu Asp Asp Ala Leu Gln Thr Asp Leu Lys Lys Leu Gln Arg Asn Pro
690                 695                 700
Pro Ile Val Lys Met Pro Arg Val Ser Asp Leu Leu Asn Thr His Pro
705                 710                 715                 720
Leu Val Gly Ala Leu Pro Ala Ala Val Arg Asp Pro Leu Leu Ser Asn
                725                 730                 735
Thr Lys Glu Thr Val Arg Gly Gln Gly Thr Thr Leu Tyr Arg Glu Gly
            740                 745                 750
Ser Arg Pro Thr Gly Ile Trp Leu Val Ser Ile Gly Val Val Lys Trp
        755                 760                 765
Thr Ser Gln Arg Leu Ser Arg Arg His Cys Leu Asp Pro Ile Leu Ser
770                 775                 780
His Gly Ser Thr Leu Gly Leu Tyr Glu Val Leu Ile Gly Lys Pro Tyr
785                 790                 795                 800
Ile Cys Asp Met Thr Thr Asp Ser Val Ala His Cys Phe Phe Ile Glu
                805                 810                 815
Thr Glu Lys Ile Glu Glu Leu Arg His Ser Asp Pro Ser Ile Glu Val
            820                 825                 830
Phe Leu Trp Gln Glu Ser Ala Leu Val Leu Ala Arg Leu Leu Leu Pro
        835                 840                 845
Arg Ile Phe Glu Lys Met Gly Met His Glu Met Arg Val Leu Ile Ala
850                 855                 860
```

```
Glu Arg Ser Thr Met Asn Ile Tyr Ile Lys Gly Glu Asp Leu Glu Val
865                 870                 875                 880

Glu Glu Asn Cys Ile Gly Ile Leu Leu Glu Gly Phe Leu Lys Thr Asp
            885                 890                 895

Asn Leu Thr Leu Ile Thr Pro Pro Ala Val Leu Leu Pro Ser Asp Ala
        900                 905                 910

Asp Leu Gly Leu Glu Ser Ser Asp Tyr Cys His Thr Ala Pro Arg Tyr
        915                 920                 925

Gln Val Glu Ala Arg Ala Arg Ile Ile Phe Leu Glu Glu Ala Glu Ala
        930                 935                 940

His Leu His Arg Ser Ala Ser Arg Leu Leu Leu Pro Gln Gly Gln Gly
945                 950                 955                 960

Gly Gly His Glu Pro Thr Arg Ser Met Ser Lys Glu His Ser Gly Leu
            965                 970                 975

Leu Ser Trp Pro Glu Ser Phe Arg Arg Ser Arg Gly Asn Leu Gly Leu
            980                 985                 990

Ala Ala Glu Met Leu Pro Gly Gly Leu Ser Ser Arg Ala Leu Gln Leu
            995                 1000                1005

Ser Met Tyr Gly Ser Met Val Ile Leu Ser Ser Gly Gln Gly His
    1010                1015                1020

Ser His Arg Arg Gln Gly Arg His Arg Val Gln Ala Thr Thr Thr
    1025                1030                1035

Asp Gln Lys Gln Ser Ser Ser Tyr Pro Arg Met Pro Ser Ile Ser
    1040                1045                1050

Lys Glu Arg Pro Leu Leu Ser Val Gln Ser Glu Gly Ser Asn Met
    1055                1060                1065

Lys Arg Val Ala Ala Leu Pro Leu Arg Asp Asp Ala Ala Glu Val
    1070                1075                1080

Glu Ala Pro Ala Ala Gln Gln Arg Arg Arg Arg Lys Ala Met His
    1085                1090                1095

Leu Gln Glu Asp Asn Ser Ser Asp Asp Ser Ala Gly Glu Glu Val
    1100                1105                1110

Ile Val Arg Val Asp Ser Pro Ser Met Leu Ser Phe Arg Gln Ser
    1115                1120                1125

Ala Ala Ala Pro Pro Pro Gln Asp Gln
    1130                1135

<210> SEQ ID NO 18
<211> LENGTH: 1148
<212> TYPE: PRT
<213> ORGANISM: Oryza sativa

<400> SEQUENCE: 18

Met Asp Asn Pro Glu Ala Glu Pro Asp Asp Ala Val Leu Phe Val Gly
1               5                   10                  15

Val Ser Leu Val Leu Gly Ile Ala Ser Arg His Leu Leu Arg Gly Thr
            20                  25                  30

Arg Val Pro Tyr Thr Val Ala Leu Leu Val Leu Gly Val Ala Leu Gly
        35                  40                  45

Ser Leu Glu Phe Gly Thr Lys His Gly Met Gly Lys Leu Gly Ala Gly
    50                  55                  60

Ile Arg Ile Trp Ala Asn Ile Asn Pro Asp Leu Leu Leu Ala Val Phe
65                  70                  75                  80
```

Leu Pro Ala Leu Leu Phe Glu Ser Ser Phe Ser Met Glu Ile His Gln
                85                  90                  95

Ile Lys Lys Cys Met Ala Gln Met Val Leu Leu Ala Gly Pro Gly Val
            100                 105                 110

Leu Ile Ser Thr Phe Phe Leu Gly Ser Ala Leu Lys Leu Thr Phe Pro
        115                 120                 125

Tyr Asn Trp Asn Trp Lys Thr Ser Leu Leu Leu Gly Gly Leu Leu Ser
    130                 135                 140

Ala Thr Asp Pro Val Ala Val Val Ala Leu Leu Lys Glu Leu Gly Ala
145                 150                 155                 160

Ser Lys Lys Leu Ser Thr Ile Ile Glu Gly Glu Ser Leu Met Asn Asp
                165                 170                 175

Gly Thr Ala Ile Val Val Tyr Gln Leu Phe Tyr Arg Met Val Leu Gly
            180                 185                 190

Arg Thr Phe Asp Ala Gly Ser Ile Ile Lys Phe Leu Ser Glu Val Ser
        195                 200                 205

Leu Gly Ala Val Ala Leu Gly Leu Ala Phe Gly Ile Ala Ser Val Leu
    210                 215                 220

Trp Leu Gly Phe Ile Phe Asn Asp Thr Ile Ile Glu Ile Ala Leu Thr
225                 230                 235                 240

Leu Ala Val Ser Tyr Ile Ala Phe Phe Thr Ala Gln Asp Ala Leu Glu
                245                 250                 255

Val Ser Gly Val Leu Thr Val Met Thr Leu Gly Met Phe Tyr Ala Ala
            260                 265                 270

Phe Ala Lys Thr Ala Phe Lys Gly Asp Ser Gln Gln Ser Leu His His
        275                 280                 285

Phe Trp Glu Met Val Ala Tyr Ile Ala Asn Thr Leu Ile Phe Ile Leu
    290                 295                 300

Ser Gly Val Val Ile Ala Asp Gly Val Leu Glu Asn Asn Val His Phe
305                 310                 315                 320

Glu Arg His Gly Ala Ser Trp Gly Phe Leu Leu Leu Leu Tyr Val Phe
                325                 330                 335

Val Gln Ile Ser Arg Ile Leu Val Val Val Ile Leu Tyr Pro Leu Leu
            340                 345                 350

Arg His Phe Gly Tyr Gly Leu Asp Leu Lys Glu Ala Thr Ile Leu Val
        355                 360                 365

Trp Ala Gly Leu Arg Gly Ala Val Ala Leu Ser Leu Ser Leu Ser Val
    370                 375                 380

Lys Arg Ala Ser Asp Ala Val Gln Thr His Leu Lys Pro Val Asp Gly
385                 390                 395                 400

Thr Met Phe Val Phe Phe Thr Gly Gly Ile Val Phe Leu Thr Leu Ile
                405                 410                 415

Phe Asn Gly Ser Thr Thr Gln Phe Leu Leu His Leu Leu Gly Met Asp
            420                 425                 430

Arg Leu Ala Ala Thr Lys Leu Arg Ile Leu Asn Tyr Thr Lys Tyr Glu
        435                 440                 445

Met Leu Asn Lys Ala Leu Glu Ala Phe Gly Asp Leu Arg Asp Asp Glu
    450                 455                 460

Glu Leu Gly Pro Pro Ala Asp Trp Val Thr Val Lys Lys Tyr Ile Thr
465                 470                 475                 480

Cys Leu Asn Asp Leu Asp Asp Glu Pro Val His Pro His Ala Val Ser
                485                 490                 495

```
Asp Arg Asn Asp Arg Met His Thr Met Asn Leu Arg Asp Ile Arg Val
                500                 505                 510

Arg Leu Leu Asn Gly Val Gln Ala Ala Tyr Trp Gly Met Leu Glu Glu
        515                 520                 525

Gly Arg Ile Thr Gln Thr Thr Ala Asn Ile Leu Met Arg Ser Val Asp
    530                 535                 540

Glu Ala Met Asp Leu Val Pro Thr Gln Glu Leu Cys Asp Trp Lys Gly
545                 550                 555                 560

Leu Arg Ser Asn Val His Phe Pro Asn Tyr Tyr Arg Phe Leu Gln Met
                565                 570                 575

Ser Arg Leu Pro Arg Arg Leu Ile Thr Tyr Phe Thr Val Glu Arg Leu
        580                 585                 590

Glu Ser Gly Cys Tyr Ile Cys Ala Ala Phe Leu Arg Ala His Arg Ile
    595                 600                 605

Ala Arg Arg Gln Leu His Asp Phe Leu Gly Asp Ser Glu Val Ala Arg
610                 615                 620

Ile Val Ile Asp Glu Ser Asn Ala Glu Gly Glu Glu Ala Arg Lys Phe
625                 630                 635                 640

Leu Glu Asp Val Arg Val Thr Phe Pro Gln Val Leu Arg Val Leu Lys
                645                 650                 655

Thr Arg Gln Val Thr Tyr Ser Val Leu Thr His Leu Ser Glu Tyr Ile
        660                 665                 670

Gln Asn Leu Gln Lys Thr Gly Leu Leu Glu Glu Lys Glu Met Ala His
    675                 680                 685

Leu Asp Asp Ala Leu Gln Thr Asp Leu Lys Lys Phe Lys Arg Asn Pro
690                 695                 700

Pro Leu Val Lys Met Pro Arg Val Ser Asp Leu Leu Asn Thr His Pro
705                 710                 715                 720

Leu Val Gly Ala Leu Pro Ala Ala Met Arg Asp Pro Leu Leu Ser Ser
                725                 730                 735

Thr Lys Glu Thr Val Lys Gly His Gly Thr Ile Leu Tyr Arg Glu Gly
        740                 745                 750

Ser Arg Pro Thr Gly Ile Trp Leu Val Ser Ile Gly Val Val Lys Trp
    755                 760                 765

Thr Ser Gln Arg Leu Ser Ser Arg His Ser Leu Asp Pro Ile Leu Ser
770                 775                 780

His Gly Ser Thr Leu Gly Leu Tyr Glu Val Leu Ile Gly Lys Pro Tyr
785                 790                 795                 800

Ile Cys Asp Met Ile Thr Asp Ser Val Val His Cys Phe Phe Ile Glu
                805                 810                 815

Ala Glu Lys Ile Glu Gln Leu Arg Gln Ser Asp Pro Ser Ile Glu Ile
        820                 825                 830

Phe Leu Trp Gln Glu Ser Ala Leu Val Val Ala Arg Leu Leu Leu Pro
    835                 840                 845

Met Met Phe Glu Lys Met Ala Thr His Glu Leu Arg Val Leu Ile Thr
850                 855                 860

Glu Arg Ser Thr Met Asn Ile Tyr Ile Lys Gly Glu Glu Ile Glu Leu
865                 870                 875                 880

Glu Gln Asn Phe Ile Gly Ile Leu Leu Glu Gly Phe Leu Lys Thr Lys
                885                 890                 895

Asn Gln Thr Leu Ile Thr Pro Pro Gly Leu Leu Leu Pro Pro Asn Ala
        900                 905                 910
```

```
Asp Leu Asn Leu Phe Gly Leu Glu Ser Ser Ala Ile Asn Arg Ile Asp
        915                 920                 925

Tyr Cys Tyr Thr Ala Pro Ser Tyr Gln Val Glu Ala Arg Ala Arg Ile
930                 935                 940

Leu Phe Val Glu Ile Gly Arg Pro Glu Ile Glu Ala Asp Leu Gln Arg
945                 950                 955                 960

Ser Ala Ser Leu Ile Ser Gln Thr Leu Glu Leu Pro Arg Thr Gln Ser
            965                 970                 975

Lys Glu His Ser Gly Leu Leu Ser Trp Pro Glu Ser Phe Arg Lys Ser
        980                 985                 990

Arg Gly Ala Gln Asn Gly Ala Ser Leu Thr Glu Ile Arg Asp His Pro
    995                 1000                1005

Ala Ser Phe Ser Ala Arg Ala Leu Gln Leu Ser Met Tyr Gly Ser
    1010                1015                1020

Met Ile Asn Asp Met Lys Ser Gly Gln Gly Gln Gly Gln Arg Arg
    1025                1030                1035

Gln Arg His Arg His Thr Lys Ala Ser Ser Asn Lys Ala His Ser
    1040                1045                1050

Ser Ser Tyr Pro Arg Val Pro Ser Arg Ser Ser Asn Thr Gln Arg
    1055                1060                1065

Pro Leu Leu Ser Val Gln Ser Glu Gly Ala Asn Met Thr Thr Ala
    1070                1075                1080

Arg Gln Ala Ala Ala Ala Gly Ala Ser Leu Pro Pro Glu Pro Glu
    1085                1090                1095

Glu Ala Gly Arg Arg Arg Arg Gln Arg Lys Ala Ile Glu Glu
    1100                1105                1110

Asp Glu Asp Asn Ser Ser Asp Glu Ser Ala Gly Glu Glu Val Ile
    1115                1120                1125

Val Arg Val Asp Ser Pro Ser Met Leu Thr Phe Arg Gln Pro Ser
    1130                1135                1140

Ser Ala Ala Asp Arg
    1145

<210> SEQ ID NO 19
<211> LENGTH: 1149
<212> TYPE: PRT
<213> ORGANISM: Glycine max

<400> SEQUENCE: 19

Val Ser Ala Ala Ser Ser Ser Glu Glu Asn Ser Asn Pro Ser Asp
1               5                   10                  15

Ala Val Ile Phe Phe Gly Leu Ser Leu Ala Leu Gly Ile Ala Cys Arg
            20                  25                  30

His Leu Leu Arg Gly Thr Arg Val Pro Tyr Thr Val Ala Leu Leu Ile
        35                  40                  45

Leu Gly Ile Ala Leu Gly Ser Ile Glu Tyr Gly Thr His His Arg Leu
    50                  55                  60

Gly Lys Ile Gly Asp Gly Ile Arg Ile Trp Ser Glu Ile Asp Pro Asp
65                  70                  75                  80

Leu Leu Leu Ala Val Phe Leu Pro Ala Leu Leu Phe Glu Ser Ser Phe
                85                  90                  95

Leu Met Glu Val His Gln Ile Lys Arg Cys Leu Ala Gln Met Ile Leu
            100                 105                 110
```

```
Leu Ala Gly Pro Gly Val Ala Leu Ser Thr Val Cys Leu Gly Val Val
        115                 120                 125

Leu Lys Leu Thr Phe Pro Tyr Asn Trp Ser Trp Lys Thr Ser Leu Leu
        130                 135                 140

Leu Gly Gly Leu Leu Ser Ala Thr Asp Pro Val Ala Val Val Ala Leu
145                 150                 155                 160

Leu Lys Asp Leu Gly Ala Ser Lys Lys Leu Ser Thr Ile Ile Glu Gly
                165                 170                 175

Glu Ser Leu Met Asn Asp Gly Thr Ala Ile Val Val Tyr Thr Leu Phe
                180                 185                 190

Tyr Arg Met Val Leu Gly Glu Thr Phe Asn Trp Val Ala Ile Ile Lys
        195                 200                 205

Phe Leu Ala Gln Val Ser Leu Gly Ala Val Gly Met Gly Leu Ala Phe
        210                 215                 220

Gly Ile Ala Ser Val Leu Trp Leu Gly Phe Ile Phe Asn Asp Thr Val
225                 230                 235                 240

Ile Glu Ile Ala Leu Thr Phe Ala Val Ser Tyr Ile Ala Tyr Phe Thr
                245                 250                 255

Ala Gln Glu Gly Ser Gly Val Ser Gly Val Leu Thr Val Met Ser Leu
                260                 265                 270

Gly Met Phe Tyr Ser Ala Phe Ala Arg Thr Ala Phe Lys Gly Glu Ser
        275                 280                 285

Gln Gln Ser Leu His His Phe Trp Glu Met Ile Ala Tyr Ile Ala Asn
        290                 295                 300

Thr Leu Ile Phe Ile Leu Ser Gly Val Val Ile Ala Glu Gly Ile Leu
305                 310                 315                 320

Gly Asp Glu Asn Val Phe Tyr His Gly Thr Ser Trp Thr His Leu Leu
                325                 330                 335

Leu Leu Tyr Ala Tyr Val Gln Val Ser Arg Cys Ile Val Val Gly Ala
                340                 345                 350

Leu Phe Pro Phe Leu Arg Tyr Phe Gly Tyr Gly Leu Asp Trp Lys Glu
        355                 360                 365

Ala Ile Ile Leu Ile Trp Ser Gly Leu Arg Gly Ala Val Ala Leu Ala
        370                 375                 380

Leu Ser Leu Ser Val Lys Ala Met Leu Leu Ile Asp Ile Ile Leu Pro
385                 390                 395                 400

Gly His Cys Thr Leu Ser Leu Phe Thr Ser Glu Ile Gly Ala Arg Ser
                405                 410                 415

Gly Gly Lys Ser Ser Glu Leu Thr Pro Glu Thr Gly Thr Leu Phe Val
                420                 425                 430

Phe Phe Thr Gly Gly Thr Val Phe Leu Thr Leu Ile Ile Asn Gly Ser
        435                 440                 445

Thr Thr Gln Phe Ile Leu His Tyr Leu Gly Met Asp Lys Leu Ser Ala
        450                 455                 460

Ala Lys Arg Arg Ile Leu Asn Phe Thr Lys Tyr Glu Met Leu Asn Lys
465                 470                 475                 480

Ala Leu Glu Ala Phe Gly Glu Leu Gly Asp Asp Glu Glu Leu Gly Pro
                485                 490                 495

Ala Asp Trp Pro Thr Val Lys Arg Tyr Ile Ser Cys Leu Asn Asp Ile
                500                 505                 510

Glu Gly Glu Cys Val His Pro His Gly Ala Pro Glu Asn Asp Ser Asn
        515                 520                 525
```

-continued

```
Leu Asp Pro Met Asn Leu Lys Asp Ile Arg Val Arg Leu Leu Asn Gly
    530                 535                 540
Val Gln Ala Ala Tyr Trp Glu Met Leu Asp Glu Gly Arg Ile Ser Gln
545                 550                 555                 560
Thr Thr Ala Asn Ile Leu Met Leu Ser Val Glu Glu Ala Val Asp Leu
                565                 570                 575
Ala Ser Ser Glu Pro Leu Cys Asp Trp Lys Gly Leu Lys Ser Asn Val
            580                 585                 590
His Phe Pro Asn Tyr Tyr Lys Phe Leu Gln Ser Ser Met Phe Pro Pro
        595                 600                 605
Lys Leu Val Thr Tyr Phe Thr Val Glu Arg Leu Glu Ser Ala Cys Tyr
    610                 615                 620
Ile Cys Ala Ala Phe Leu Arg Ala His Arg Ile Ala Arg Gln Gln Leu
625                 630                 635                 640
His Asp Phe Ile Gly Asp Ser Asp Ile Ala Ser Ala Val Ile Asn Glu
                645                 650                 655
Ser Val Val Glu Gly Glu Glu Ala Arg Lys Phe Leu Glu Asp Val Asn
            660                 665                 670
Val Thr Tyr Pro Gln Val Leu Arg Val Val Lys Thr Arg Gln Ala Thr
        675                 680                 685
Tyr Ala Val Leu Asn His Leu Ile Glu Tyr Val Glu Asn Leu Glu Lys
    690                 695                 700
Ala Gly Ile Leu Glu Glu Lys Glu Met Leu Gln Leu His Asp Ala Val
705                 710                 715                 720
Gln Thr Asp Leu Lys Lys Leu Leu Arg Asn Pro Pro Leu Val Lys Leu
                725                 730                 735
Pro Lys Ile Ser Ser Ile His Pro Met Leu Gly Ala Leu Pro Ser Ser
            740                 745                 750
Val Arg Glu Ser Leu Ala Ser Cys Thr Lys Glu Met Met Lys Leu Arg
        755                 760                 765
Gly Leu Thr Leu Tyr Lys Glu Gly Ala Lys Ser Asn Gly Ile Trp Leu
    770                 775                 780
Ile Ser Asn Gly Val Val Lys Trp Glu Ser Lys Met Ile Arg Thr Lys
785                 790                 795                 800
His Ser Phe Asn Pro Thr Phe Thr His Gly Ser Thr Leu Gly Ile Tyr
                805                 810                 815
Glu Val Leu Thr Gly Arg Ser Tyr Ile Cys Asp Val Val Thr Asp Ser
            820                 825                 830
Val Val Phe Cys Ile Phe Leu Glu Ala Asp Lys Ile Arg Ser Cys Leu
        835                 840                 845
Lys Ala Asp Pro Leu Thr Glu Lys Phe Leu Trp Glu Ser Ala Ile
    850                 855                 860
Phe Leu Ser Lys Leu Leu Leu Pro Gln Ile Phe Glu Lys Leu Gly Met
865                 870                 875                 880
Gln Asp Leu Arg Thr Leu Ile Ala Asp Ser Glu Arg Ser Arg Met Thr
                885                 890                 895
Ile Phe Ile Arg Gly Glu Thr Ile Glu Ile Pro His Ser Val Ala
            900                 905                 910
Leu Leu Leu Glu Gly Tyr Val Lys Thr Gln Gly Arg Gln Glu Leu Val
        915                 920                 925
Thr Ala Pro Ala Ala Leu Leu Pro Ser His Gly Asn Leu Ser Phe Gln
    930                 935                 940
```

-continued

Asn Leu Ala Ser Ser Gly Ser Lys Glu Ala Ser Phe Ile His Gln Gln
945                 950                 955                 960

Gly Ser Ser Tyr Leu Val Glu Thr Thr Ala Arg Val Ile Leu Phe Asp
                965                 970                 975

Ile Pro Ala Pro Glu Ala Asp Ala Ala Leu Val Arg Arg Ser Ser Ser
            980                 985                 990

Leu Leu Ser His Ala Gly Asp His Pro His Arg Ser Phe Arg Arg Lys
        995                 1000                1005

His Ser Gly Leu Met Ser Trp Pro Glu His Phe Tyr Lys Gln Asp
    1010                1015                1020

His Lys Gln Arg Ser Glu Gly Ala Gly Arg Gln Thr Asn Ser Leu
    1025                1030                1035

Ser Ala Arg Ala Met Gln Leu Ser Ile Tyr Gly Ser Met Met Phe
    1040                1045                1050

Phe Ile Asn Val Glu Asn Gln Ile Pro Asp His Thr Leu Lys Arg
    1055                1060                1065

Gln Cys Tyr Leu Ser Ser Met Pro His His Ile Gly Val Cys Arg
    1070                1075                1080

Pro Leu Val Ser Val Lys Ser Glu Gly Ala Ala Thr Ala Lys Lys
    1085                1090                1095

Val His Glu Val Thr Arg His Val Thr Asn Pro Pro Ser Gln Ser
    1100                1105                1110

Thr Glu Arg Arg Gln His His His Gly Asp Asn Ser Ser Asp Asp
    1115                1120                1125

Ser Gly Ala Glu Glu Glu Asp Ile Ile Val Arg Ile Asp Ser Pro
    1130                1135                1140

Ser Thr Leu Ser Phe Arg
    1145

<210> SEQ ID NO 20
<211> LENGTH: 1146
<212> TYPE: PRT
<213> ORGANISM: Arabidopsis thaliana

<400> SEQUENCE: 20

Met Thr Thr Val Ile Asp Ala Thr Met Ala Tyr Arg Phe Leu Glu Glu
1               5                   10                  15

Ala Thr Asp Ser Ser Ser Ser Ser Ser Ser Lys Leu Glu Ser Ser
                20                  25                  30

Pro Val Asp Ala Val Leu Phe Val Gly Met Ser Leu Val Leu Gly Ile
            35                  40                  45

Ala Ser Arg His Leu Leu Arg Gly Thr Arg Val Pro Tyr Thr Val Ala
        50                  55                  60

Leu Leu Val Ile Gly Ile Ala Leu Gly Ser Leu Glu Tyr Gly Ala Lys
65                  70                  75                  80

His Asn Leu Gly Lys Ile Gly His Gly Ile Arg Ile Trp Asn Glu Ile
                85                  90                  95

Asp Pro Glu Leu Leu Leu Ala Val Phe Leu Pro Ala Leu Leu Phe Glu
            100                 105                 110

Ser Ser Phe Ser Met Glu Val His Gln Ile Lys Arg Cys Leu Gly Gln
        115                 120                 125

Met Val Leu Leu Ala Val Pro Gly Val Leu Ile Ser Thr Ala Cys Leu
130                 135                 140

-continued

```
Gly Ser Leu Val Lys Val Thr Phe Pro Tyr Glu Trp Asp Trp Lys Thr
145                 150                 155                 160

Ser Leu Leu Leu Gly Leu Leu Ser Ala Thr Asp Pro Val Ala Val
            165                 170                 175

Val Ala Leu Leu Lys Glu Leu Gly Ala Ser Lys Lys Leu Ser Thr Ile
            180                 185                 190

Ile Glu Gly Glu Ser Leu Met Asn Asp Gly Thr Ala Ile Val Val Phe
            195                 200                 205

Gln Leu Phe Leu Lys Met Ala Met Gly Gln Asn Ser Asp Trp Ser Ser
210                 215                 220

Ile Ile Lys Phe Leu Leu Lys Val Ala Leu Gly Ala Val Gly Ile Gly
225                 230                 235                 240

Leu Ala Phe Gly Ile Ala Ser Val Ile Trp Leu Lys Phe Ile Phe Asn
                245                 250                 255

Asp Thr Val Ile Glu Ile Thr Leu Thr Ile Ala Val Ser Tyr Phe Ala
            260                 265                 270

Tyr Tyr Thr Ala Gln Glu Trp Ala Gly Ala Ser Gly Val Leu Thr Val
        275                 280                 285

Met Thr Leu Gly Met Phe Tyr Ala Ala Phe Ala Arg Thr Ala Phe Lys
290                 295                 300

Gly Asp Ser Gln Lys Ser Leu His His Phe Trp Glu Met Val Ala Tyr
305                 310                 315                 320

Ile Ala Asn Thr Leu Ile Phe Ile Leu Ser Gly Val Val Ile Ala Glu
                325                 330                 335

Gly Ile Leu Asp Ser Asp Lys Ile Ala Tyr Gln Gly Asn Ser Trp Arg
            340                 345                 350

Phe Leu Phe Leu Leu Tyr Val Tyr Ile Gln Leu Ser Arg Val Val Val
        355                 360                 365

Val Gly Val Leu Tyr Pro Leu Leu Cys Arg Phe Gly Tyr Gly Leu Asp
    370                 375                 380

Trp Lys Glu Ser Ile Ile Leu Val Trp Ser Gly Leu Arg Gly Ala Val
385                 390                 395                 400

Ala Leu Ala Leu Ser Leu Ser Val Lys Gln Ser Ser Gly Asn Ser His
                405                 410                 415

Ile Ser Lys Glu Thr Gly Thr Leu Phe Leu Phe Phe Thr Gly Gly Ile
            420                 425                 430

Val Phe Leu Thr Leu Ile Val Asn Gly Ser Thr Thr Gln Phe Val Leu
        435                 440                 445

Arg Leu Leu Arg Met Asp Ile Leu Pro Ala Pro Lys Lys Arg Ile Leu
    450                 455                 460

Glu Tyr Thr Lys Tyr Glu Met Leu Asn Lys Ala Leu Arg Ala Phe Gln
465                 470                 475                 480

Asp Leu Gly Asp Asp Glu Glu Leu Gly Pro Ala Asp Trp Pro Thr Val
                485                 490                 495

Glu Ser Tyr Ile Ser Ser Leu Lys Gly Ser Gly Glu Leu Val His
            500                 505                 510

His Pro His Asn Gly Ser Lys Ile Gly Ser Leu Asp Pro Lys Ser Leu
        515                 520                 525

Lys Asp Ile Arg Met Arg Phe Leu Asn Gly Val Gln Ala Thr Tyr Trp
    530                 535                 540

Glu Met Leu Asp Glu Gly Arg Ile Ser Glu Val Thr Ala Asn Ile Leu
545                 550                 555                 560
```

```
Met Gln Ser Val Asp Glu Ala Leu Asp Gln Val Ser Thr Thr Leu Cys
                565                 570                 575
Asp Trp Arg Gly Leu Lys Pro His Val Asn Phe Pro Asn Tyr Tyr Asn
            580                 585                 590
Phe Leu His Ser Lys Val Val Pro Arg Lys Leu Val Thr Tyr Phe Ala
            595                 600                 605
Val Glu Arg Leu Glu Ser Ala Cys Tyr Ile Ser Ala Phe Leu Arg
        610                 615                 620
Ala His Thr Ile Ala Arg Gln Gln Leu Tyr Asp Phe Leu Gly Glu Ser
625                 630                 635                 640
Asn Ile Gly Ser Ile Val Ile Asn Glu Ser Glu Lys Glu Gly Glu Glu
                645                 650                 655
Ala Lys Lys Phe Leu Glu Lys Val Arg Ser Ser Phe Pro Gln Val Leu
                660                 665                 670
Arg Val Val Lys Thr Lys Gln Val Thr Tyr Ser Val Leu Asn His Leu
            675                 680                 685
Leu Gly Tyr Ile Glu Asn Leu Glu Lys Val Gly Leu Leu Glu Glu Lys
        690                 695                 700
Glu Ile Ala His Leu His Asp Ala Val Gln Thr Gly Leu Lys Lys Leu
705                 710                 715                 720
Leu Arg Asn Pro Pro Ile Val Lys Leu Pro Lys Leu Ser Asp Met Ile
                725                 730                 735
Thr Ser His Pro Leu Ser Val Ala Leu Pro Pro Ala Phe Cys Glu Pro
            740                 745                 750
Leu Lys His Ser Lys Lys Glu Pro Met Lys Leu Arg Gly Val Thr Leu
            755                 760                 765
Tyr Lys Glu Gly Ser Lys Pro Thr Gly Val Trp Leu Ile Phe Asp Gly
        770                 775                 780
Ile Val Lys Trp Lys Ser Lys Ile Leu Ser Asn Asn His Ser Leu His
785                 790                 795                 800
Pro Thr Phe Ser His Gly Ser Thr Leu Gly Leu Tyr Glu Val Leu Thr
                805                 810                 815
Gly Lys Pro Tyr Leu Cys Asp Leu Ile Thr Asp Ser Met Val Leu Cys
            820                 825                 830
Phe Phe Ile Asp Ser Glu Lys Ile Leu Ser Leu Gln Ser Asp Ser Thr
            835                 840                 845
Ile Asp Asp Phe Leu Trp Gln Glu Ser Ala Leu Val Leu Leu Lys Leu
        850                 855                 860
Leu Arg Pro Gln Ile Phe Glu Ser Val Ala Met Gln Glu Leu Arg Ala
865                 870                 875                 880
Leu Val Ser Thr Glu Ser Ser Lys Leu Thr Thr Tyr Val Thr Gly Glu
                885                 890                 895
Ser Ile Glu Ile Asp Cys Asn Ser Ile Gly Leu Leu Glu Gly Phe
            900                 905                 910
Val Lys Pro Val Gly Ile Lys Glu Glu Leu Ile Ser Ser Pro Ala Ala
            915                 920                 925
Leu Ser Pro Ser Asn Gly Asn Gln Ser Phe His Asn Ser Ser Glu Ala
        930                 935                 940
Ser Gly Ile Met Arg Val Ser Phe Ser Gln Gln Ala Thr Gln Tyr Ile
945                 950                 955                 960
Val Glu Thr Arg Ala Arg Ala Ile Ile Phe Asn Ile Gly Ala Phe Gly
                965                 970                 975
```

```
Ala Asp Arg Thr Leu His Arg Arg Pro Ser Ser Leu Thr Pro Pro Arg
            980                 985                 990

Ser Ser Ser Ser Asp Gln Leu Gln Arg Ser Phe Arg Lys Glu His Arg
        995                 1000                1005

Gly Leu Met Ser Trp Pro Glu Asn Ile Tyr Ala Lys Gln Gln Gln
    1010                1015                1020

Glu Ile Asn Lys Thr Thr Leu Ser Leu Ser Glu Arg Ala Met Gln
    1025                1030                1035

Leu Ser Ile Phe Gly Ser Met Val Asn Val Tyr Arg Arg Ser Val
    1040                1045                1050

Ser Phe Gly Gly Ile Tyr Asn Asn Lys Leu Gln Asp Asn Leu Leu
    1055                1060                1065

Tyr Lys Lys Leu Pro Leu Asn Pro Ala Gln Gly Leu Val Ser Ala
    1070                1075                1080

Lys Ser Glu Ser Ser Ile Val Thr Lys Lys Gln Leu Glu Thr Arg
    1085                1090                1095

Lys His Ala Cys Gln Leu Pro Leu Lys Gly Glu Ser Ser Thr Arg
    1100                1105                1110

Gln Asn Thr Met Val Glu Ser Ser Asp Glu Glu Asp Glu Asp Glu
    1115                1120                1125

Gly Ile Val Val Arg Ile Asp Ser Pro Ser Lys Ile Val Phe Arg
    1130                1135                1140

Asn Asp Leu
    1145

<210> SEQ ID NO 21
<211> LENGTH: 756
<212> TYPE: PRT
<213> ORGANISM: Arabidopsis thaliana

<400> SEQUENCE: 21

Met Thr Ser Ile Ile Gly Ala Ala Leu Pro Tyr Lys Ser Pro Glu Lys
1               5                   10                  15

Ala Ile Ala Ser Ser Ser Tyr Ser Ala Glu Asn Asp Ser Ser Pro Val
            20                  25                  30

Asp Ala Val Ile Phe Ala Gly Thr Ser Leu Val Leu Gly Thr Ala Cys
        35                  40                  45

Arg Tyr Leu Phe Asn Gly Thr Arg Val Pro Tyr Thr Val Val Leu Leu
    50                  55                  60

Val Ile Gly Ile Phe Leu Gly Ser Leu Glu Tyr Gly Thr Lys His Asn
65                  70                  75                  80

Leu Gly Lys Leu Gly His Gly Ile Arg Ile Trp Asn Gly Ile Asn Pro
                85                  90                  95

Asp Leu Leu Leu Ala Val Phe Leu Pro Val Leu Leu Phe Glu Ser Ser
            100                 105                 110

Phe Ser Met Asp Val His Gln Ile Lys Arg Cys Met Gly Gln Met Val
        115                 120                 125

Leu Leu Ala Gly Pro Gly Val Leu Ile Ser Thr Phe Cys Leu Gly Ala
    130                 135                 140

Leu Ile Lys Leu Thr Phe Pro Tyr Asn Trp Asp Trp Lys Thr Ser Leu
145                 150                 155                 160

Leu Leu Gly Gly Leu Leu Gly Ala Thr Asp Pro Val Ala Val Val Ala
                165                 170                 175
```

```
Leu Leu Lys Glu Leu Gly Ala Ser Lys Lys Met Thr Thr Leu Ile Asp
            180                 185                 190

Gly Glu Ser Leu Met Asn Asp Gly Val Ser Val Val Phe Gln Leu
        195                 200                 205

Phe Phe Lys Met Val Met Gly His Asn Ser Asp Trp Gly Ser Ile Ile
        210                 215                 220

Lys Phe Leu Val Gln Asn Ser Phe Gly Ala Val Gly Ile Gly Leu Ala
225                 230                 235                 240

Phe Gly Ile Ala Ser Val Phe Trp Leu Lys Phe Ile Phe Asn Asp Thr
                245                 250                 255

Val Ala Gln Ile Thr Val Thr Leu Ser Ala Ser Tyr Phe Ala Tyr Tyr
            260                 265                 270

Thr Ala Gln Glu Trp Ala Gly Val Ser Gly Ile Leu Thr Val Met Ile
        275                 280                 285

Leu Gly Met Phe Phe Ala Ala Phe Ala Arg Thr Ala Phe Lys Gly Asp
        290                 295                 300

Ser His Gln Ser Leu His His Phe Trp Glu Met Ala Ala Tyr Ile Ala
305                 310                 315                 320

Asn Thr Leu Val Phe Met Leu Ser Gly Val Ile Ile Ala Glu Ser Val
                325                 330                 335

Leu Ser Gly Gln Thr Ile Ser Tyr Lys Gly Asn Ser Trp Ser Phe Leu
            340                 345                 350

Phe Leu Leu Tyr Leu Tyr Val Gln Leu Ser Arg Cys Val Val Val Gly
        355                 360                 365

Val Leu Tyr Pro Leu Leu Cys Arg Ser Gly Tyr Gly Leu Asp Trp Lys
        370                 375                 380

Glu Ser Ile Ile Leu Thr Trp Ser Gly Leu Arg Gly Ala Val Ser Leu
385                 390                 395                 400

Ser Leu Ala Leu Ser Val Lys Gln Ser Ser Gly Asn Ser Tyr Leu Ser
                405                 410                 415

Ser Asp Thr Gly Thr Arg Phe Leu Phe Leu Thr Gly Gly Ile Val Phe
            420                 425                 430

Leu Thr Leu Val Val Asn Gly Ser Thr Thr Gln Leu Leu Leu His Leu
        435                 440                 445

Leu Arg Met Asp Thr Leu Thr Ala Thr Lys Lys Arg Ile Leu Glu Tyr
        450                 455                 460

Thr Lys Phe Glu Met Met Lys Thr Ala Leu Lys Ala Phe Glu Asn Leu
465                 470                 475                 480

Gly Asp Asp Glu Glu Leu Gly Ser Ala Asp Trp Pro Thr Val Ile Arg
                485                 490                 495

His Ile Ser Ser Leu Lys Asp Leu Glu Gly Arg Gln Val Asn Pro His
            500                 505                 510

Asp Gly Tyr Glu Ala Gly Ser Leu Asp Pro Thr Asn Ile Met Asp Ile
        515                 520                 525

Arg Ile Arg Phe Leu Asn Gly Val Gln Ala Ala Tyr Trp Glu Met Leu
        530                 535                 540

Asp Asp Gly Arg Ile Thr Gln Cys Thr Ala Asn Val Leu Met Gln Ser
545                 550                 555                 560

Val Asp Glu Ala Leu Asp Leu Val Ser Thr Ser Ser Leu Ser Asp Trp
                565                 570                 575

Arg Gly Leu Glu Pro Arg Val His Phe Pro Asn Tyr Tyr Lys Phe Leu
            580                 585                 590
```

-continued

```
Gln Ser Lys Ile Ile Pro His Lys Leu Val Thr His Leu Ile Val Glu
            595                 600                 605

Arg Leu Glu Ser Ala Cys Tyr Ile Ser Ser Ala Phe Leu Arg Ala His
        610                 615                 620

Arg Ile Ala Arg Gln Gln Leu His Ile Phe Leu Gly Asn Ser Asn Ile
625                 630                 635                 640

Ala Ser Thr Val Ile Asn Glu Ser Glu Val Glu Gly Glu Glu Ala Lys
                645                 650                 655

Gln Phe Leu Glu Asp Val Arg Asp Ser Phe Pro Gln Val Leu Ser Val
            660                 665                 670

Leu Lys Thr Arg Gln Val Thr His Tyr Val Leu Asn His Leu Asn Gly
        675                 680                 685

Tyr Ile Lys Asn Leu Glu Lys Val Gly Leu Leu Glu Gly Lys Glu Val
690                 695                 700

Ser His Leu His Asp Val Val Gln Ser Asp Leu Lys Lys Leu Leu Arg
705                 710                 715                 720

His Pro Pro Ser Leu Lys Leu Pro Asn Val Asp Asp Leu Ile Thr Ser
                725                 730                 735

Asn Pro Leu Leu Lys Asp Arg Ser Ser Phe Arg Ser Leu Ala Ile Gly
            740                 745                 750

Glu Thr Asp Ala
            755

<210> SEQ ID NO 22
<211> LENGTH: 1093
<212> TYPE: PRT
<213> ORGANISM: Zea mays

<400> SEQUENCE: 22

Met Gly Gly Glu Ala Glu Pro Asp Asn Ala Val Leu Phe Val Gly Val
1               5                   10                  15

Ser Leu Val Leu Gly Ile Ala Ser Arg His Leu Leu Arg Gly Thr Arg
            20                  25                  30

Val Pro Tyr Thr Val Ala Leu Leu Val Leu Gly Val Ala Leu Gly Ser
        35                  40                  45

Leu Glu Tyr Gly Thr Gln His Gly Leu Gly Lys Leu Gly Ala Gly Ile
    50                  55                  60

Arg Ile Trp Ala Asn Ile Asn Pro Asp Leu Leu Leu Ala Val Phe Leu
65                  70                  75                  80

Pro Ala Leu Leu Phe Glu Ser Ser Phe Ser Met Glu Val His Gln Ile
                85                  90                  95

Lys Arg Cys Met Ala Gln Met Val Leu Leu Ala Gly Pro Gly Val Leu
            100                 105                 110

Ile Ser Thr Val Leu Leu Gly Val Ala Val Lys Leu Thr Phe Pro Tyr
        115                 120                 125

Asn Trp Ser Trp Lys Thr Ser Leu Leu Leu Gly Gly Leu Leu Ser Ala
    130                 135                 140

Thr Asp Pro Val Ala Val Val Ala Leu Leu Lys Glu Leu Gly Ala Ser
145                 150                 155                 160

Lys Lys Leu Ser Thr Ile Ile Glu Gly Glu Ser Leu Met Asn Asp Gly
                165                 170                 175

Thr Ala Ile Val Ala Tyr Gln Leu Phe Tyr Arg Met Val Leu Gly Arg
            180                 185                 190

Thr Phe Asp Ala Gly Ser Ile Ile Lys Phe Leu Ser Glu Val Ser Leu
        195                 200                 205
```

Gly Ala Val Ala Leu Gly Leu Ala Phe Gly Ile Met Ser Ile Leu Trp
            210                 215                 220

Leu Gly Phe Ile Phe Asn Asp Thr Ile Ile Glu Ile Ala Leu Thr Leu
225                 230                 235                 240

Ala Val Ser Tyr Ile Ala Phe Phe Thr Ala Gln Asp Ser Leu Glu Val
                245                 250                 255

Ser Gly Val Leu Thr Val Met Thr Leu Gly Met Phe Tyr Ala Ala Phe
            260                 265                 270

Ala Lys Thr Ala Phe Lys Gly Glu Ser Gln Gln Ser Leu His His Phe
        275                 280                 285

Trp Glu Met Val Ala Tyr Ile Ala Asn Thr Leu Ile Phe Ile Leu Ser
        290                 295                 300

Gly Val Val Ile Ala Asp Gly Val Leu Gln Asn Asn Gly His Phe Glu
305                 310                 315                 320

Arg His Gly Ser Ser Trp Gly Phe Leu Leu Leu Tyr Val Phe Val
                325                 330                 335

Gln Ile Ser Arg Val Ile Val Val Gly Val Leu Tyr Pro Met Leu Arg
                340                 345                 350

His Phe Gly Tyr Gly Leu Asp Leu Lys Glu Ala Met Ile Leu Val Trp
            355                 360                 365

Ser Gly Leu Arg Gly Ala Val Ala Leu Ser Leu Ser Leu Ser Val Lys
370                 375                 380

Arg Thr Ser Asp Ser Val Gln Pro Tyr Leu Lys Pro Glu Val Gly Thr
385                 390                 395                 400

Met Phe Val Phe Phe Thr Gly Gly Ile Val Phe Leu Thr Leu Ile Phe
                405                 410                 415

Asn Gly Ser Thr Thr Gln Phe Leu Leu His Ile Leu Gly Met Asp Lys
            420                 425                 430

Leu Leu Pro Thr Lys Leu Arg Ile Leu Lys Tyr Thr Arg Tyr Glu Met
        435                 440                 445

Leu Lys Lys Ala Leu Glu Ala Phe Gly Glu Leu Arg Asp Asp Glu Glu
        450                 455                 460

Leu Gly Pro Ala Asp Trp Val Thr Val Lys Lys Tyr Ile Thr Cys Leu
465                 470                 475                 480

Asn Asp Leu Asp Tyr Glu Pro His Pro His Asp Val Gly Asp Glu
                485                 490                 495

Asp Asp Cys Met His Ile Met Asn Leu Thr Asp Ile Arg Val Arg Leu
            500                 505                 510

Leu Asn Gly Val Gln Ala Ala Tyr Trp Gly Met Leu Glu Glu Gly Arg
        515                 520                 525

Ile Thr Gln Val Thr Ala Asn Ile Leu Met Arg Ser Val Asp Glu Ala
        530                 535                 540

Met Asp Leu Val Ser Gly Gln Thr Leu Cys Asp Trp Lys Gly Leu Lys
545                 550                 555                 560

Ser Asn Val Gln Phe Pro Asn Tyr Tyr Arg Phe Leu Gln Arg Ser Arg
                565                 570                 575

Leu Pro Arg Lys Leu Val Thr Tyr Phe Thr Val Glu Arg Leu Glu Ser
            580                 585                 590

Gly Cys Tyr Ile Cys Ala Ala Phe Leu Arg Ala His Arg Ile Ala Arg
        595                 600                 605

Arg Gln Leu His Asp Phe Leu Gly Asp Ser Glu Val Ala Arg Thr Val
610                 615                 620

-continued

```
Ile Asp Glu Ser Asn Ala Glu Gly Glu Glu Ala Arg Lys Phe Leu Glu
625                 630                 635                 640

Asp Val Arg Val Thr Phe Pro Gln Val Leu Arg Val Leu Lys Thr Arg
            645                 650                 655

Gln Val Thr Tyr Ser Val Leu Thr His Leu Ser Glu Tyr Ile Gln Asn
        660                 665                 670

Leu Gln Lys Thr Gly Leu Leu Glu Glu Lys Glu Met Val His Leu Asp
    675                 680                 685

Asp Ala Leu Gln Thr Asp Leu Lys Lys Leu Gln Arg Asn Pro Pro Ile
690                 695                 700

Val Lys Met Pro Arg Val Ser Asp Leu Leu Asn Thr His Pro Leu Val
705                 710                 715                 720

Gly Ala Leu Pro Ala Ala Val Arg Asp Thr Leu Leu Ser Asn Thr Lys
            725                 730                 735

Glu Thr Leu Arg Gly Gln Gly Thr Thr Leu Tyr Arg Glu Gly Ser Arg
        740                 745                 750

Pro Thr Gly Ile Trp Leu Val Ser Ile Gly Val Val Lys Trp Thr Ser
    755                 760                 765

Gln Arg Leu Ser Arg Arg His Ser Leu Asp Pro Ile Leu Ser His Gly
770                 775                 780

Ser Thr Leu Gly Leu Tyr Glu Val Leu Ile Gly Lys Pro Tyr Ile Cys
785                 790                 795                 800

Asp Met Thr Thr Asp Ser Met Val Gln Cys Phe Phe Ile Glu Thr Glu
            805                 810                 815

Lys Ile Glu Glu Leu Leu His Ser Asp Pro Ser Ile Glu Ile Phe Leu
        820                 825                 830

Trp Gln Glu Ser Ala Leu Val Leu Ala Arg Leu Leu Val Pro His Arg
    835                 840                 845

Phe Glu Lys Met Gly Met His Glu Met Arg Val Leu Val Ala Glu Arg
850                 855                 860

Ser Thr Met Asn Ile Tyr Ile Lys Gly Glu Asp Leu Glu Val Glu Gln
865                 870                 875                 880

Asn Cys Ile Gly Ile Leu Leu Glu Gly Phe Leu Lys Ile Glu Asn Leu
            885                 890                 895

Thr Leu Ile Thr Pro Pro Ala Leu Leu Leu Pro Trp Asn Ala Asp Leu
        900                 905                 910

Ser Leu Phe Gly Leu Glu Ser Ser Asp Tyr Cys His Thr Ala Arg Arg
    915                 920                 925

Tyr Gln Val Glu Ala Arg Ala Arg Ile Ile Phe Phe Asp Glu Ala Glu
930                 935                 940

Ala Ala His Leu His Val Gln Thr Ser Ala Ser Leu Pro Gln Gly Glu
945                 950                 955                 960

Pro Ala Arg Ser Met Ser Lys Glu His Ser Gly Leu Leu Ser Trp Pro
            965                 970                 975

Glu Ser Phe Arg Arg Ser Arg Gly Ser Leu Gly Leu Ala Ala Glu Met
        980                 985                 990

Leu Pro Gly Gly Leu Ser Ser Arg  Ala Leu Gln Leu Ser  Met Tyr Gly
    995                 1000                1005

Gly Ser  Val Val Ser Leu Ser  Ser Gly Gln Gln Gly  His Arg Arg
    1010                1015                1020

Gln Arg  Pro Arg His Arg Val  Gln Ala Ala Thr Thr  Met Thr Asn
    1025                1030                1035
```

Gln Lys Lys His Ser Ser Ser Tyr Pro Arg Met Pro Ser Ile Ser
    1040                1045                1050

Lys Glu Arg His Leu Leu Ser Val Gln Ser Glu Gly Ser Asn Met
1055                    1060                1065

Glu Trp Gln Leu Tyr Leu Arg Leu Leu Pro Pro Leu Leu Leu Arg
1070                    1075                1080

Gln Gly Gln His Arg Gly Ser Gly Gly Leu
    1085                1090

<210> SEQ ID NO 23
<211> LENGTH: 1280
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(77)

```
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (94)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (118)..(119)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (126)..(127)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (138)..(139)
<223> OTHER INFORMATION: Xaa can be any naturally occurring amino acid
<220> FEATURE:
<221> NAME/KEY: misc_feature
<222> LOCATION: (142)..(143)
<223> OTHER INFORMATION: Xaa can be any naturally occurring amino acid
<220> FEATURE:
<221> NAME/KEY: misc_feature
<222> LOCATION: (146)..(148)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
```

```
<222> LOCATION: (157)..(157)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (203)..(205)
<223> OTHER INFORMATION: Xaa can be any naturally occurring amino acid
<220> FEATURE:
<221> NAME/KEY: misc_feature
<222> LOCATION: (207)..(209)
<223> OTHER INFORMATION: Xaa can be any naturally occurring amino acid
<220> FEATURE:
<221> NAME/KEY: misc_feature
<222> LOCATION: (212)..(213)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:
<221> NAME/KEY: misc_feature
<222> LOCATION: (218)..(224)
<223> OTHER INFORMATION: Xaa can be any naturally occurring amino acid
<220> FEATURE:
<221> NAME/KEY: misc_feature
<222> LOCATION: (230)..(234)
<223> OTHER INFORMATION: Xaa can be any naturally occurring amino acid
<220> FEATURE:
<221> NAME/KEY: misc_feature
<222> LOCATION: (238)..(239)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(249)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (259)..(261)
<223> OTHER INFORMATION: Xaa can be any naturally occurring amino acid
<220> FEATURE:
<221> NAME/KEY: misc_feature
<222> LOCATION: (263)..(264)
<223> OTHER INFORMATION: Xaa can be any naturally occurring amino acid
<220> FEATURE:
<221> NAME/KEY: misc_feature
<222> LOCATION: (266)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
```

```
<221> NAME/KEY: misc_feature
<222> LOCATION: (273)..(274)
<223> OTHER INFORMATION: Xaa can be any naturally occurring amino acid
<220> FEATURE:
<221> NAME/KEY: misc_feature
<222> LOCATION: (278)..(282)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (295)..(296)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (308)..(309)
<223> OTHER INFORMATION: Xaa can be any naturally occurring amino acid
<220> FEATURE:
<221> NAME/KEY: misc_feature
<222> LOCATION: (316)..(379)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (400)..(402)
<223> OTHER INFORMATION: Xaa can be any naturally occurring amino acid
<220> FEATURE:
<221> NAME/KEY: misc_feature
<222> LOCATION: (404)..(412)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (417)..(418)
<223> OTHER INFORMATION: Xaa can be any naturally occurring amino acid
<220> FEATURE:
<221> NAME/KEY: misc_feature
<222> LOCATION: (420)..(420)
<223> OTHER INFORMATION: Xaa can be any naturally occurring amino acid
<220> FEATURE:
<221> NAME/KEY: misc_feature
<222> LOCATION: (424)..(426)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
```

```
<220> FEATURE:
<221> NAME/KEY: misc_feature
<222> LOCATION: (431)..(432)
<223> OTHER INFORMATION: Xaa can be any naturally occurring amino acid
<220> FEATURE:
<221> NAME/KEY: misc_feature
<222> LOCATION: (435)..(436)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (442)..(444)
<223> OTHER INFORMATION: Xaa can be any naturally occurring amino acid
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: misc_feature
<222> LOCATION: (453)..(454)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (466)..(466)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (475)..(499)
<223> OTHER INFORMATION: Xaa can be any naturally occurring amino acid
<220> FEATURE:
<221> NAME/KEY: misc_feature
<222> LOCATION: (501)..(511)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (522)..(522)
<223> OTHER INFORMATION: Xaa can be any naturally occurring amino acid
<220> FEATURE:
<221> NAME/KEY: misc_feature
<222> LOCATION: (528)..(529)
<223> OTHER INFORMATION: Xaa can be any naturally occurring amino acid
<220> FEATURE:
<221> NAME/KEY: misc_feature
<222> LOCATION: (536)..(537)
```

```
<223> OTHER INFORMATION: Xaa can be any naturally occurring amino acid
<220> FEATURE:
<221> NAME/KEY: misc_feature
<222> LOCATION: (539)..(540)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (547)..(549)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (555)..(556)
<223> OTHER INFORMATION: Xaa can be any naturally occurring amino acid
<220> FEATURE:
<221> NAME/KEY: misc_feature
<222> LOCATION: (558)..(559)
<223> OTHER INFORMATION: Xaa can be any naturally occurring amino acid
<220> FEATURE:
<221> NAME/KEY: misc_feature
<222> LOCATION: (562)..(564)
<223> OTHER INFORMATION: Xaa can be any naturally occurring amino acid
<220> FEATURE:
<221> NAME/KEY: misc_feature
<222> LOCATION: (567)..(568)
<223> OTHER INFORMATION: Xaa can be any naturally occurring amino acid
<220> FEATURE:
<221> NAME/KEY: misc_feature
<222> LOCATION: (570)..(571)
<223> OTHER INFORMATION: Xaa can be any naturally occurring amino acid
<220> FEATURE:
<221> NAME/KEY: misc_feature
<222> LOCATION: (573)..(573)
<223> OTHER INFORMATION: Xaa can be any naturally occurring amino acid
<220> FEATURE:
<221> NAME/KEY: misc_feature
<222> LOCATION: (580)..(581)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (588)..(590)
<223> OTHER INFORMATION: Xaa can be any naturally occurring amino acid
<220> FEATURE:
<221> NAME/KEY: misc_feature
<222> LOCATION: (592)..(593)
<223> OTHER INFORMATION: Xaa can be any naturally occurring amino acid
<220> FEATURE:
<221> NAME/KEY: misc_feature
<222> LOCATION: (595)..(604)
<223> OTHER INFORMATION: Xaa can be any naturally occurring amino acid
<220> FEATURE:
<221> NAME/KEY: misc_feature
<222> LOCATION: (607)..(621)
<223> OTHER INFORMATION: Xaa can be any naturally occurring amino acid
<220> FEATURE:
<221> NAME/KEY: misc_feature
<222> LOCATION: (625)..(625)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
```

-continued

```
<222> LOCATION: (634)..(634)
<223> OTHER INFORMATION: Xaa can be any naturally occurring amino acid
<220> FEATURE:
<221> NAME/KEY: misc_feature
<222> LOCATION: (637)..(637)
<223> OTHER INFORMATION: Xaa can be any naturally occurring amino acid
<220> FEATURE:
<221> NAME/KEY: misc_feature
<222> LOCATION: (640)..(641)
<223> OTHER INFORMATION: Xaa can be any naturally occurring amino acid
<220> FEATURE:
<221> NAME/KEY: misc_feature
<222> LOCATION: (645)..(647)
<223> OTHER INFORMATION: Xaa can be any naturally occurring amino acid
<220> FEATURE:
<221> NAME/KEY: misc_feature
<222> LOCATION: (651)..(651)
<223> OTHER INFORMATION: Xaa can be any naturally occurring amino acid
<220> FEATURE:
<221> NAME/KEY: misc_feature
<222> LOCATION: (654)..(654)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (662)..(667)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (675)..(677)
<223> OTHER INFORMATION: Xaa can be any naturally occurring amino acid
<220> FEATURE:
<221> NAME/KEY: misc_feature
<222> LOCATION: (679)..(679)
<223> OTHER INFORMATION: Xaa can be any naturally occurring amino acid
<220> FEATURE:
<221> NAME/KEY: misc_feature
<222> LOCATION: (685)..(685)
<223> OTHER INFORMATION: Xaa can be any naturally occurring amino acid
<220> FEATURE:
<221> NAME/KEY: misc_feature
<222> LOCATION: (688)..(692)
<223> OTHER INFORMATION: Xaa can be any naturally occurring amino acid
<220> FEATURE:
<221> NAME/KEY: misc_feature
<222> LOCATION: (694)..(695)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (699)..(701)
<223> OTHER INFORMATION: Xaa can be any naturally occurring amino acid
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (712)..(713)
<223> OTHER INFORMATION: Xaa can be any naturally occurring amino acid
<220> FEATURE:
```

```
<221> NAME/KEY: misc_feature
<222> LOCATION: (720)..(720)
<223> OTHER INFORMATION: Xaa can be any naturally occurring amino acid
<220> FEATURE:
<221> NAME/KEY: misc_feature
<222> LOCATION: (724)..(724)
<223> OTHER INFORMATION: Xaa can be any naturally occurring amino acid
<220> FEATURE:
<221> NAME/KEY: misc_feature
<222> LOCATION: (727)..(728)
<223> OTHER INFORMATION: Xaa can be any naturally occurring amino acid
<220> FEATURE:
<221> NAME/KEY: misc_feature
<222> LOCATION: (730)..(730)
<223> OTHER INFORMATION: Xaa can be any naturally occurring amino acid
<220> FEATURE:
<221> NAME/KEY: misc_feature
<222> LOCATION: (732)..(732)
<223> OTHER INFORMATION: Xaa can be any naturally occurring amino acid
<220> FEATURE:
<221> NAME/KEY: misc_feature
<222> LOCATION: (734)..(738)
<223> OTHER INFORMATION: Xaa can be any naturally occurring amino acid
<220> FEATURE:
<221> NAME/KEY: misc_feature
<222> LOCATION: (741)..(741)
<223> OTHER INFORMATION: Xaa can be any naturally occurring amino acid
<220> FEATURE:
<221> NAME/KEY: misc_feature
<222> LOCATION: (744)..(745)
<223> OTHER INFORMATION: Xaa can be any naturally occurring amino acid
<220> FEATURE:
<221> NAME/KEY: misc_feature
<222> LOCATION: (751)..(752)
<223> OTHER INFORMATION: Xaa can be any naturally occurring amino acid
<220> FEATURE:
<221> NAME/KEY: misc_feature
<222> LOCATION: (756)..(756)
<223> OTHER INFORMATION: Xaa can be any naturally occurring amino acid
<220> FEATURE:
<221> NAME/KEY: misc_feature
<222> LOCATION: (758)..(761)
<223> OTHER INFORMATION: Xaa can be any naturally occurring amino acid
<220> FEATURE:
<221> NAME/KEY: misc_feature
<222> LOCATION: (766)..(766)
<223> OTHER INFORMATION: Xaa can be any naturally occurring amino acid
<220> FEATURE:
<221> NAME/KEY: misc_feature
<222> LOCATION: (768)..(768)
<223> OTHER INFORMATION: Xaa can be any naturally occurring amino acid
<220> FEATURE:
<221> NAME/KEY: misc_feature
<222> LOCATION: (771)..(771)
<223> OTHER INFORMATION: Xaa can be any naturally occurring amino acid
<220> FEATURE:
<221> NAME/KEY: misc_feature
<222> LOCATION: (773)..(773)
<223> OTHER INFORMATION: Xaa can be any naturally occurring amino acid
<220> FEATURE:
<221> NAME/KEY: misc_feature
<222> LOCATION: (775)..(776)
<223> OTHER INFORMATION: Xaa can be any naturally occurring amino acid
<220> FEATURE:
<221> NAME/KEY: misc_feature
<222> LOCATION: (779)..(779)
<223> OTHER INFORMATION: Xaa can be any naturally occurring amino acid
<220> FEATURE:
<221> NAME/KEY: misc_feature
<222> LOCATION: (782)..(783)
<223> OTHER INFORMATION: Xaa can be any naturally occurring amino acid
<220> FEATURE:
<221> NAME/KEY: misc_feature
<222> LOCATION: (785)..(786)
<223> OTHER INFORMATION: Xaa can be any naturally occurring amino acid
<220> FEATURE:
<221> NAME/KEY: misc_feature
<222> LOCATION: (789)..(789)
<223> OTHER INFORMATION: Xaa can be any naturally occurring amino acid
```

```
<220> FEATURE:
<221> NAME/KEY: misc_feature
<222> LOCATION: (791)..(791)
<223> OTHER INFORMATION: Xaa can be any naturally occurring amino acid
<220> FEATURE:
<221> NAME/KEY: misc_feature
<222> LOCATION: (793)..(793)
<223> OTHER INFORMATION: Xaa can be any naturally occurring amino acid
<220> FEATURE:
<221> NAME/KEY: misc_feature
<222> LOCATION: (796)..(796)
<223> OTHER INFORMATION: Xaa can be any naturally occurring amino acid
<220> FEATURE:
<221> NAME/KEY: misc_feature
<222> LOCATION: (799)..(801)
<223> OTHER INFORMATION: Xaa can be any naturally occurring amino acid
<220> FEATURE:
<221> NAME/KEY: misc_feature
<222> LOCATION: (803)..(803)
<223> OTHER INFORMATION: Xaa can be any naturally occurring amino acid
<220> FEATURE:
<221> NAME/KEY: misc_feature
<222> LOCATION: (805)..(806)
<223> OTHER INFORMATION: Xaa can be any naturally occurring amino acid
<220> FEATURE:
<221> NAME/KEY: misc_feature
<222> LOCATION: (808)..(809)
<223> OTHER INFORMATION: Xaa can be any naturally occurring amino acid
<220> FEATURE:
<221> NAME/KEY: misc_feature
<222> LOCATION: (813)..(814)
<223> OTHER INFORMATION: Xaa can be any naturally occurring amino acid
<220> FEATURE:
<221> NAME/KEY: misc_feature
<222> LOCATION: (816)..(816)
<223> OTHER INFORMATION: Xaa can be any naturally occurring amino acid
<220> FEATURE:
<221> NAME/KEY: misc_feature
<222> LOCATION: (819)..(820)
<223> OTHER INFORMATION: Xaa can be any naturally occurring amino acid
<220> FEATURE:
<221> NAME/KEY: misc_feature
<222> LOCATION: (822)..(822)
<223> OTHER INFORMATION: Xaa can be any naturally occurring amino acid
<220> FEATURE:
<221> NAME/KEY: misc_feature
<222> LOCATION: (824)..(946)
<223> OTHER INFORMATION: Xaa can be any naturally occurring amino acid
<220> FEATURE:
<221> NAME/KEY: misc_feature
<222> LOCATION: (948)..(950)
<223> OTHER INFORMATION: Xaa can be any naturally occurring amino acid
<220> FEATURE:
<221> NAME/KEY: misc_feature
<222> LOCATION: (952)..(963)
<223> OTHER INFORMATION: Xaa can be any naturally occurring amino acid
<220> FEATURE:
<221> NAME/KEY: misc_feature
<222> LOCATION: (965)..(1280)
<223> OTHER INFORMATION: Xaa can be any naturally occurring amino acid

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Pro Xaa Xaa Ala Val Xaa Phe Xaa Gly Xaa Ser Leu Xaa Leu Gly Xaa
        35                  40                  45

Ala Xaa Arg Xaa Leu Xaa Xaa Gly Thr Arg Val Pro Tyr Thr Val Xaa
    50                  55                  60

Leu Leu Xaa Xaa Gly Xaa Xaa Leu Gly Ser Xaa Glu Xaa Gly Xaa Xaa
65                  70                  75                  80
```

```
His Xaa Xaa Gly Lys Xaa Gly Xaa Gly Ile Arg Ile Trp Xaa Xaa Ile
                85              90                  95

Xaa Pro Xaa Leu Leu Leu Ala Val Phe Leu Pro Xaa Leu Leu Phe Glu
            100                 105                 110

Ser Ser Phe Xaa Met Xaa Xaa His Gln Ile Lys Xaa Cys Xaa Xaa Gln
            115                 120                 125

Met Xaa Leu Leu Ala Xaa Pro Gly Val Xaa Xaa Ser Thr Xaa Xaa Leu
    130                 135                 140

Gly Xaa Xaa Xaa Lys Xaa Thr Phe Pro Tyr Xaa Trp Xaa Trp Lys Thr
145             150                 155                     160

Ser Leu Leu Leu Gly Gly Leu Leu Xaa Ala Thr Asp Pro Val Ala Val
                165                 170                 175

Val Ala Leu Leu Lys Xaa Leu Gly Ala Ser Lys Lys Xaa Xaa Thr Xaa
            180                 185                 190

Ile Xaa Gly Glu Ser Leu Met Asn Asp Gly Xaa Xaa Xaa Val Xaa Xaa
        195                 200                 205

Xaa Leu Phe Xaa Xaa Met Xaa Xaa Gly Xaa Xaa Xaa Xaa Xaa Xaa Xaa
    210                 215                 220

Ile Ile Lys Phe Leu Xaa Xaa Xaa Xaa Gly Ala Val Xaa Xaa Gly
225             230                 235                 240

Leu Ala Phe Gly Ile Xaa Ser Xaa Xaa Trp Leu Xaa Phe Ile Phe Asn
                245                 250                 255

Asp Thr Xaa Xaa Xaa Ile Xaa Xaa Thr Xaa Xaa Xaa Ser Tyr Xaa Ala
            260                 265                 270

Xaa Xaa Thr Ala Gln Xaa Xaa Xaa Xaa Ser Gly Xaa Leu Thr Val
        275                 280                 285

Met Xaa Leu Gly Met Phe Xaa Xaa Ala Phe Ala Xaa Thr Ala Phe Lys
    290                 295                 300

Gly Xaa Ser Xaa Xaa Ser Leu His His Phe Trp Xaa Xaa Xaa Xaa Xaa
305             310                 315                     320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Glu Met Xaa Ala Tyr
    370                 375                 380

Ile Ala Asn Thr Leu Xaa Phe Xaa Leu Ser Gly Val Xaa Ile Ala Xaa
385             390                 395                     400

Xaa Xaa Leu Xaa Xaa Xaa Xaa Xaa Xaa Xaa Xaa Gly Xaa Ser Trp
            405                 410                 415

Xaa Xaa Leu Xaa Leu Leu Tyr Xaa Xaa Xaa Gln Xaa Ser Arg Xaa Xaa
            420                 425                 430

Val Val Xaa Xaa Leu Xaa Pro Xaa Leu Xaa Xaa Xaa Gly Tyr Gly Leu
            435                 440                 445

Asp Xaa Lys Glu Xaa Xaa Ile Leu Xaa Trp Xaa Gly Leu Arg Gly Ala
    450                 455                 460

Val Xaa Leu Xaa Leu Xaa Leu Ser Val Lys Xaa Xaa Xaa Xaa Xaa
465             470                 475                 480

Xaa Xaa Xaa Xaa Xaa Xaa Xaa Xaa Xaa Xaa Xaa Xaa Xaa Xaa Xaa
            485                 490                 495
```

```
Xaa Xaa Xaa Ser Xaa Xaa Xaa Xaa Xaa Xaa Xaa Xaa Gly
            500             505             510

Th

-continued

Xaa Xaa Xaa Xaa Xaa Xaa Xaa Xaa Xaa Xaa Xaa Xaa Xaa Xaa Xaa
    915                 920                 925

Xaa Xaa Xaa Xaa Xaa Xaa Xaa Xaa Xaa Xaa Xaa Xaa Xaa Xaa Xaa
    930                 935                 940

Xaa Xaa Leu Xaa Xaa Xaa Ser Xaa Xaa Xaa Xaa Xaa Xaa Xaa Xaa
945                 950                 955                 960

Xaa Xaa Xaa Phe Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa Xaa Xaa Xaa Xaa Xaa Xaa Xaa
        995                 1000                1005

Xaa Xaa Xaa Xaa Xaa Xaa Xaa Xaa Xaa Xaa Xaa Xaa Xaa Xaa Xaa
    1010                1015                1020

Xaa Xaa Xaa Xaa Xaa Xaa Xaa Xaa Xaa Xaa Xaa Xaa Xaa Xaa Xaa
    1025                1030                1035

Xaa Xaa Xaa Xaa Xaa Xaa Xaa Xaa Xaa Xaa Xaa Xaa Xaa Xaa Xaa
    1040                1045                1050

Xaa Xaa Xaa Xaa Xaa Xaa Xaa Xaa Xaa Xaa Xaa Xaa Xaa Xaa Xaa
    1055                1060                1065

Xaa Xaa Xaa Xaa Xaa Xaa Xaa Xaa Xaa Xaa Xaa Xaa Xaa Xaa Xaa
    1070                1075                1080

Xaa Xaa Xaa Xaa Xaa Xaa Xaa Xaa Xaa Xaa Xaa Xaa Xaa Xaa Xaa
    1085                1090                1095

Xaa Xaa Xaa Xaa Xaa Xaa Xaa Xaa Xaa Xaa Xaa Xaa Xaa Xaa Xaa
    1100                1105                1110

Xaa Xaa Xaa Xaa Xaa Xaa Xaa Xaa Xaa Xaa Xaa Xaa Xaa Xaa Xaa
    1115                1120                1125

Xaa Xaa Xaa Xaa Xaa Xaa Xaa Xaa Xaa Xaa Xaa Xaa Xaa Xaa Xaa
    1130                1135                1140

Xaa Xaa Xaa Xaa Xaa Xaa Xaa Xaa Xaa Xaa Xaa Xaa Xaa Xaa Xaa
    1145                1150                1155

Xaa Xaa Xaa Xaa Xaa Xaa Xaa Xaa Xaa Xaa Xaa Xaa Xaa Xaa Xaa
    1160                1165                1170

Xaa Xaa Xaa Xaa Xaa Xaa Xaa Xaa Xaa Xaa Xaa Xaa Xaa Xaa Xaa
    1175                1180                1185

Xaa Xaa Xaa Xaa Xaa Xaa Xaa Xaa Xaa Xaa Xaa Xaa Xaa Xaa Xaa
    1190                1195                1200

Xaa Xaa Xaa Xaa Xaa Xaa Xaa Xaa Xaa Xaa Xaa Xaa Xaa Xaa Xaa
    1205                1210                1215

Xaa Xaa Xaa Xaa Xaa Xaa Xaa Xaa Xaa Xaa Xaa Xaa Xaa Xaa Xaa
    1220                1225                1230

Xaa Xaa Xaa Xaa Xaa Xaa Xaa Xaa Xaa Xaa Xaa Xaa Xaa Xaa Xaa
    1235                1240                1245

Xaa Xaa Xaa Xaa Xaa Xaa Xaa Xaa Xaa Xaa Xaa Xaa Xaa Xaa Xaa
    1250                1255                1260

Xaa Xaa Xaa Xaa Xaa Xaa Xaa Xaa Xaa Xaa Xaa Xaa Xaa Xaa Xaa
    1265                1270                1275

Xaa Xaa
1280

What is claimed is:

1. A method of identifying a maize plant with decreased tolerance to salt stress and/or drought, said method comprising:
   a. detecting in a maize plant a QTL allele associated with decreased tolerance to salt stress and/or drought, wherein said QTL allele comprises a 4 bp deletion in the antiporter/sodium ion transporter gene at nucleotides 3311-3314 of SEQ ID NO:15; and
   b. identifying the maize plant as having the 4 bp deletion, wherein said maize plant has decreased tolerance to salt stress and/or drought; and
   c. counter-selecting the maize plant from a breeding program.

2. A method of identifying a maize plant with tolerance to salt stress and/or drought, said method comprising:
   a. detecting in the genome of a maize plant any of the following:
      i. a polynucleotide encoding a polypeptide having the amino acid sequence set forth in SEQ ID NO:16;
      ii. a polynucleotide encoding a polypeptide having an amino acid sequence that is at least 90% identical to SEQ ID NO:16 that has antiporter/sodium ion transporter activity; or
      iii. one or more marker alleles within 5 cM of (i) or (ii) that are linked to and associated with (i) or (ii);
   b. identifying a maize plant as having tolerance to salt stress and/or drought if any of (i), (ii), or (iii) is detected, wherein said salt stress comprises soil having an electrical conductivity of at least about 2 dS/m;
   c. selecting the maize plant comprising any of (i), (ii), or (iii) and identified as having salt stress and/or drought tolerance; and
   d. breeding with the selected maize plant.

3. A method of identifying an allelic variant of an antiporter/sodium ion transporter gene wherein said allelic variant is associated with increased tolerance to salt stress and/or drought in a maize plant, the method comprising the steps of:
   a. obtaining a population of maize plants, wherein said maize plants exhibit differing levels of salt tolerance and/or drought tolerance and wherein said plants have been genotyped, wherein said salt stress comprises soil having an electrical conductivity of at least about 2 dS/m;
   b. determining allelic variations of a polynucleotide sequence encoding a protein having an amino acid sequence that is at least 90% identical to comprising SEQ ID NO:16 in the population of genotyped maize plants;
   c. associating allelic variations with increased tolerance to salt stress and/or drought;
   d. identifying an allelic variant that is associated with increased tolerance to salt stress and/or drought in a maize plant;
   e. detecting in a maize plant the presence of the allelic variant associated with increased tolerance to salt stress and/or drought;
   f. selecting the maize plant with the allelic variant; and
   g. breeding with the selected maize plant.

4. The method of claim 1, wherein said salt stress comprises soil having an electrical conductivity of at least about 2 dS/m.

* * * * *